(12) United States Patent
Koh et al.

(10) Patent No.: US 12,144,797 B2
(45) Date of Patent: Nov. 19, 2024

(54) COMPOUND FOR USE IN THE TREATMENT AND/OR PREVENTION OF PARASITIC MEDIATED DISEASES

(71) Applicants: Hwee Ling Koh, Singapore (SG); Woon Chien Cecilia Teng, Singapore (SG); Ying Lee, Singapore (SG)

(72) Inventors: Hwee Ling Koh, Singapore (SG); Woon Chien Cecilia Teng, Singapore (SG); Ying Lee, Singapore (SG)

(73) Assignee: Hwee Ling Koh, Singapore (SG)

( * ) Notice: Subject to any disclaimer, the term of this patent is extended or adjusted under 35 U.S.C. 154(b) by 0 days.

(21) Appl. No.: 16/077,359

(22) PCT Filed: Mar. 8, 2017

(86) PCT No.: PCT/SG2017/050109
§ 371 (c)(1),
(2) Date: Aug. 10, 2018

(87) PCT Pub. No.: WO2017/155465
PCT Pub. Date: Sep. 14, 2017

(65) Prior Publication Data
US 2019/0046503 A1    Feb. 14, 2019

(30) Foreign Application Priority Data
Mar. 11, 2016    (SG) .............................. 10201601898S

(51) Int. Cl.
*A61K 31/37*    (2006.01)
*A61K 36/75*    (2006.01)
*A61P 33/06*    (2006.01)

(52) U.S. Cl.
CPC .............. *A61K 31/37* (2013.01); *A61K 36/75* (2013.01); *A61P 33/06* (2018.01); *Y02A 50/30* (2018.01)

(58) Field of Classification Search
CPC ......... A61K 31/37; A61K 36/75; A61P 33/06; Y02A 50/30
See application file for complete search history.

(56) References Cited

U.S. PATENT DOCUMENTS
8,709,445 B2    4/2014    Craft et al.

FOREIGN PATENT DOCUMENTS

| CN | 103251741 A | 8/2013 |
|---|---|---|
| CN | 103598383 A | 2/2014 |
| CN | 105902449 A | 8/2016 |
| WO | 9413282 A1 | 6/1994 |

OTHER PUBLICATIONS

Liu et al (Phytochemistry, 2014; 107:141-147) (Year: 2014).*
Okokon et al (Asian Pac J Trop Med, 2012; 5(3):214-219) (Year: 2012).*
Arbab et al (J Med Plants Res, 2012; 6(38):5107-5118) (Year: 2012).*
Murungi, J. M. (2013). Antimalarial activity and safety properties of Clausena anisata and Clutia robusta in a mouse model (Doctoral dissertation) (Year: 2013).*
Lakshmi et al (Indian Drugs, 1986, 24(6): 285-287) (Year: 1986).*
Kharazmi et al (Scandinavian Journal of Immunology, 1987; 25(4):321-429) (Year: 1987).*
Shen et al (J Nat Prod, 2014; 44:1215-1223) (Year: 2014).*
Deng et al (Planta Med 2014; 80: 955-958) (Year: 2014).*
Dhankar S. et al., *Aegle mamelos* (Linn.) Correa: A potential source of Phytomedicine. j. Med. Plants Res., May 4, 2011, vol. 5, No. 9, pp. 1497-1507 [Retrieved on May 10, 2017] <DOI: 10.5897/0BA544C17458> p. 1498, 1502; Figure 1.
Dolabela M. F. et al., In vitro antiplasmodial activity of extract and constituents from *Esenbeckia febrifuga*, a plant traditionally used to treat malaria in the Brazilian Amazon. Phytomedicine, Mar. 11, 2008, vol. 15, No. 5, pp. 367-372 [Retrieved on May 10, 2017] <DOI: 10.1016/J.PHYMED.2008.02.001> Experimental section; results and discussion; Figure 1; table 1.
Makofane H. F. et al., The compounds and biological activity of Thamnosma Africana. S. Afr. J Sci. Tech., Sep. 22, 2006, vol. 25, No. 3, pp. 138-148 [Retrieved on May 10, 2017] <DOI: 10.4102/SATNT.V2513.154> Table 1; Figure 1; section 2.1, 2.3-2.5, 3.3 of the machine translation.
Li W.-S. et al., Furanocoumarins and sesquiterpene ketone from Clausena lansium skeels. j. Chin. Chem. Soc., Dec. 31, 1990, vol. 37, No. 6, pp. 571-575 [Retrieved on May 10, 2017] <DOI: 10.1002/JCCS. 199000078> Introduction; Fig 1 compounds 2 and 3; Extractiona and Crude Fractionation.

(Continued)

*Primary Examiner* — Amanda L. Aguirre
(74) *Attorney, Agent, or Firm* — JCIP; Joseph G. Chu

(57) ABSTRACT

The present invention provides a compound belonging to furanocoumarin derivative having core structure (A) as given below, its pharmaceutically acceptable salt, isomer or a combination thereof for the treatment and/or prevention of a parasitic mediated disease. The present invention also provides a method for manufacturing and isolating said compound as well as method for treatment and prevention of parasitic mediated disease using said compound. In a preferred embodiment, the parasite is *Plasmodium falciparum*, the disease mediated by the said parasite is malaria and the furanocoumarin derivative having core structure (A) is Anisolactone.

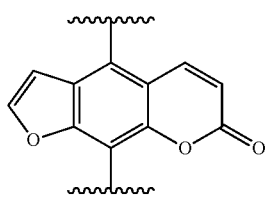

7 Claims, 9 Drawing Sheets

(56) References Cited

OTHER PUBLICATIONS

Zhang R.-M. et al., Advances in Chemical Constituents and Biological Activities of Clausena lansium. Nat Prod Res Dev, Jan. 31, 2012, vol. 24, No. 1, pp. 118-123 [Retrieved on May 10, 2017] <DOI: 10.16333/J.1001-6880.2012.01.025> Sections 1.2, 2.7, 4 of the machine translation.

Maneerat W. et al., New Coumarins from Clausena lansium Twigs. J. Braz. Chem. Soc., Jan. 31, 2010, vol. 21, No. 4, pp. 665-668 [Retrieved on May 10, 2017] <DOI: 10.1590/S0103-50532010000400012> Figure 1 compounds 1, 2, 5 and 6; p. 666 right col; Experimental.

Arbab I. A. et al., A review of traditional uses, phytochemical and pharmacological aspects of selected members of Clausena genus (Rutaceae). J. Med. Plants. Res., Oct. 3, 2012, vol. 6, No. 38, pp. 5107-5118 [Retrieved on May 10, 2017] <DOI: 10.5897/JMPR12.317> p. 5111-5112; Table 1.

Nam V. D. et al., Chemical Composition of Clausena lansium (Lour.) Skeels Leaves and Antifungal Activity. Nat. Prod. Sci., Mar. 31, 2016, vol. 22, No. 1, pp. 35-40 [Retrieved on May 10, 2017] <DOI: 10.20307/NPS.2016.22.1.35> Fig 1, Extraction and isolation in p. 37.

International Search Report and Written Opinion of ISA for International Application PCT/SG2017/050109.

Y.C. Kong et al., Gen. Pharmac. vol. 17, No. 5, pp. 593-595, 1986, "Smooth Muscle Relaxant Effect of Dehydroindicolactone".

Murugesan Susitra Manjari et al., "Chemical composition and larvicidal activity of plant extracts from Clausena dentata (Wild) (Rutaceae) against dengue, malaria, and filariasis vectors", Parasitol Res (2014) 113:2475-2481, DOI 10.1007/s00436-014-3896-7.

Y.C. Kong et al., "Dehydroindicolactone, a new Coumarin from Clausena lansium", Mar. 24, 1983.

Bioactive Furanocoumarins From Stes of Clausena Lansium, Hang liu, Fei Li, Chuang-Jun Li, Jing-Zhi Yang, Li Li, Nai-Hong Chen, Dong-Ming Zhang, Phytochemistry 107 (2014) 141-147, Elsevier ltd.

Chinese Search Report from China National Intellectual Property Administration dated Mar. 28, 2020 for Chinese Application No. 201780010896.3.

Jude E. Okokon et al., Antiplasmodial and analgesic activities of Clausena anisata, Asian Pacific Journal of Tropical Medicine, Jan. 15, 2012, pp. 214-219 Department of Pharmacology and Toxicology, Faculty of Pharmacy, University of Uyo, Ugo, Nigeria.

Ismail Adam Arbab et al., A review of traditional uses, phytochemical and pharmacological aspects of selected members of Clausena genus (Rutaceae), Journal of Medicinal Plants Research, vol. 6(38), pp. 5107-5118, Oct. 3, 2012.

* cited by examiner

COMPOUND FOR USE IN THE TREATMENT AND/OR PREVENTION OF PARASITIC MEDIATED DISEASES

FIELD OF INVENTION

The present invention relates to compounds and methods for treatment and/or prevention of parasitic mediated diseases, in particular malaria disease.

BACKGROUND TO THE INVENTION

The following discussion of the background to the invention is intended to facilitate an understanding of the present invention. However, it should be appreciated that the discussion is not an acknowledgment or admission that any of the material referred to was published, known or part of the common general knowledge in any jurisdiction as at the priority date of the application.

Most parasites that cause disease are endoparasites caused by either helminths, protozoa, bacteria or viruses. Some parasitic diseases are easily treated and some are not. The burden of these diseases often occurs in the tropics and subtropics as well as in more temperate climates. Of all parasitic diseases, malaria causes the most deaths globally, most of them are young children.

Malaria is one of the most common infectious diseases transmitted by certain species of mosquitoes of the *Anopheles* genus. Malaria disease has plagued humankind for millennia and it has been a great public health problem worldwide, particularly in tropical and subtropical regions of the world. The World Health Organization (WHO) currently estimates that malaria causes 300 to 500 million infections and over 1 million deaths each year. The causative agent of malarial disease is parasitic protozoans belonging to the *Plasmodium* genus. There are 6 parasite species responsible for malaria in humans. Of which, *Plasmodium falciparum* poses the greatest mortal threat.

Malaria is usually treated by administering chloroquine, pyrimethamine, quinine or artemisinin compounds. While there are several drugs known to be remedies to treat or prevent malaria, their effectiveness is unfortunately being increasingly threatened by parasite drug resistance. Even the recent Nobel prize-winning anti-malarial drug Artemisinin and its derivatives, arguably the last line of defence against this devastating disease, have been associated with decreased efficacy and emerging drug resistance (Ariey F. et. al. 2014, *Nature*). For this reason, there is an urgent need to discover new active compounds to ensure a sustainable pipeline of lead compounds for malarial disease. Along with this has been the desire to establish efficient methods for preparing the same.

While it is possible to prepare some of the available anti-malarial drugs via chemical synthesis such as total synthesis, the most economical and a potential source of obtaining new anti-malarial drugs are plants since they contain a quantity of natural products with a great diversity of structures and pharmacological activities.

The medicinal fruit tree *Clausena lansium* Skeels is minor member of the Rutaceae family. It is native to, and commonly cultivated in southern China (Fujian, Guangdong, Guangxi, southern Guizhou, Jinshajiang river valley in Sichuan, and Yunnan) and North to Central Vietnam. The leaves and seeds of *Clausena lansium* were first entered as medicines in the Records of Picking Herbs in Lingnan for toxin removal, rheumatismal edema, scabies and cooling. The ripe fruit of *Clausena lansium* was first described as a medicine in Compendium of Materia Medica for wound healing.

As this medicinal species was documented in most ancient herbal medicine works, many researches have isolated a large range of compounds from various parts of the plant seeking new and useful medicines. More than 80 compounds isolated from *Clausena lansium* have been reported.

SUMMARY OF THE INVENTION

It is an object of the present invention to provide a compound and/or its derivatives for treatment and/or prevention of parasitic mediated malarial disease including a method of preparing the compound for treatment of a parasitic mediated malarial disease.

Accordingly, an aspect of the present invention is to provide a method of treating and/or preventing a parasitic mediated disease in a subject, comprising administering to the subject a pharmaceutical composition comprising a furanocoumarin derivative having the following core structure (A),

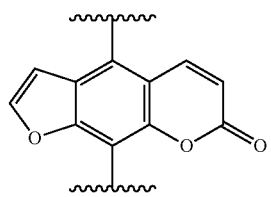

(A)

its pharmaceutical acceptable salt, isomer or a combination thereof.

Another aspect of the present invention provides a compound for use in the treatment and/or prevention of a parasitic mediated disease, the compound comprising a furanocoumarin derivative having the following core structure (A):

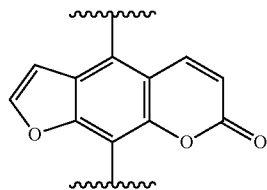

(A)

its pharmaceutical acceptable salt, isomer or a combination thereof.

Another aspect of the present invention provides a method of manufacturing a compound comprising a furanocoumarin derivative having the following core structure (A):

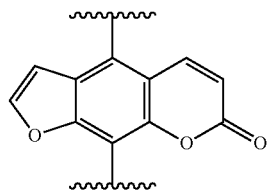

(A)

its pharmaceutical acceptable salt, isomer or a combination thereof for the treatment and/or prevention of a parasitic mediated disease.

Another aspect of the present invention provides a method of isolating a compound from the leaves of plant *Clausena lansium* comprising the step of macerating the leaves in a solvent, wherein the compound comprises a furanocoumarin derivative having the following core structure (A):

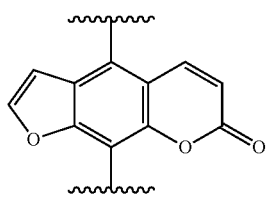

(A)

or its isomer present in the solvent.

In various embodiments, the furanocoumarin derivative has one of the following structures (1a) and (2a).

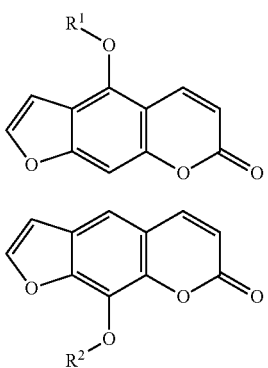

(1a)

(2a)

wherein $R^1$ is an aliphatic chain comprising a cyclic ester functional group.

In various embodiments, the furanocoumarin derivative has one of the following structures (compound (1b), (2b) or (2c)):

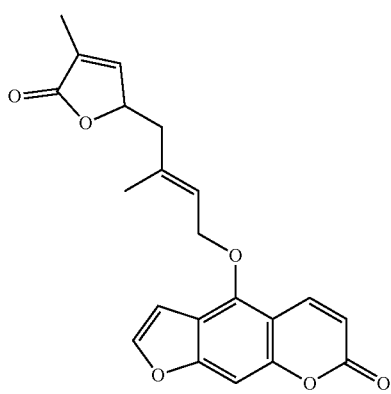

(1b)

-continued

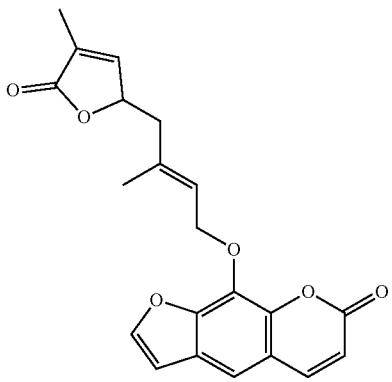

(2b)

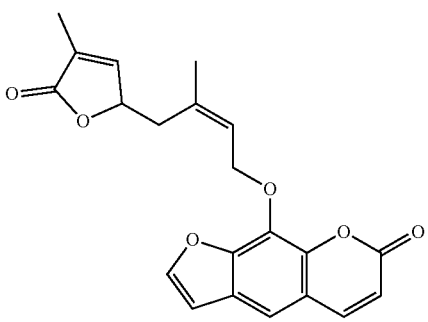

(2c)

Other aspects of the invention will become apparent to those of ordinary skill in the art upon review of the following description of specific embodiments of the invention in conjunction with the accompanying figures.

BRIEF DESCRIPTION OF THE DRAWINGS

The present invention will now be described, by way of illustrative example only, with reference to the accompanying drawings, of which.

DETAILED DESCRIPTION OF THE INVENTION

Figure 1A:
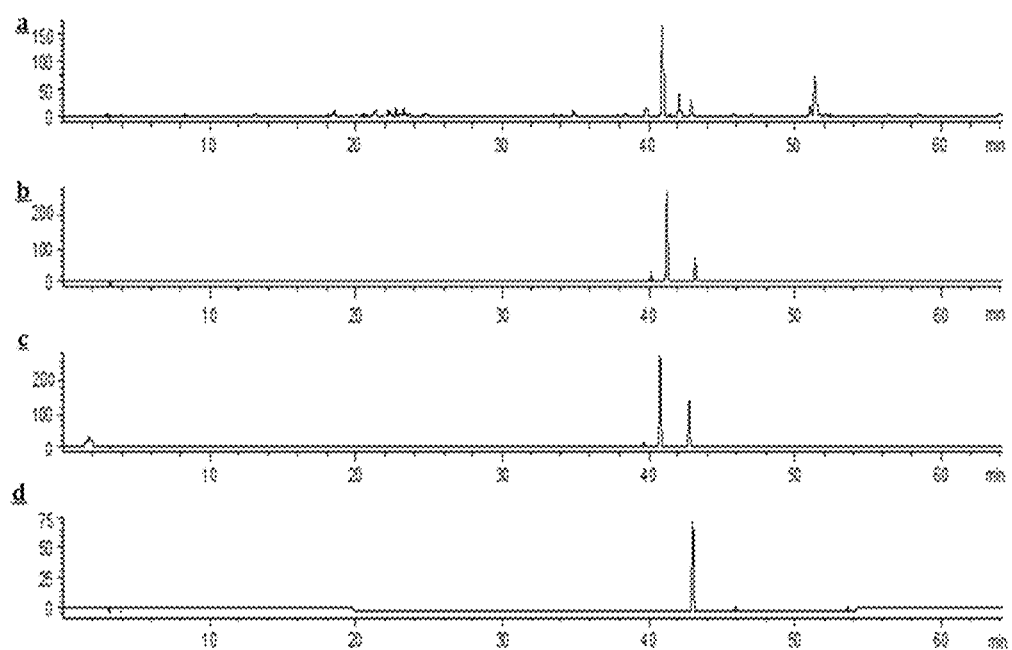
FIG. 1a shows the HPLC profiles of (a) ethanolic plant *Clausena lansium* maceration extract, (b) dichloromethane alkaloidal extract, and (c) Plant C fraction B (batch 8, 183-194) and (d) compound (1b).

Throughout this document, unless otherwise indicated to the contrary, the terms "comprising", "consisting of", "having" and the like, are to be construed as non-exhaustive, or in other words, as meaning "including, but not limited to".

Furthermore, throughout the specification, unless the context requires otherwise, the word "include" or variations such as "includes" or "including" will be understood to imply the inclusion of a stated integer or group of integers but not the exclusion of any other integer or group of integers.

Unless defined otherwise, all technical and scientific terms used herein have the same meaning as is commonly understood by a skilled person to which the subject matter herein belongs. As used herein, the following definitions are supplied in order to facilitate the understanding of the present invention.

As used in the specification, the singular form "a", "an" and "the" include plural references unless the context clearly dictates otherwise.

As used in the specification, the term "arthropod" refers to an invertebrate animal having an exoskeleton and a segmented body.

As used in the specification, the term "aliphatic chain" refers to a saturated or unsaturated carbon chain. Besides hydrogen, other elements can be bound to the carbon chain include, but are not limited to oxygen, nitrogen and sulfur.

As used in the specification, the term "double bond" refers to a chemical bond in which two pairs of electrons are shared between two atoms.

As used in the specification, the term "furanonyl" refers to a substituent comprising

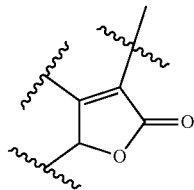 [SMILES: *C1=C(*)C(*)OC1=O]

Malaria is a significant parasitic infection for human which causative agent is the protozoan of *Plasmodium* genus. Every year around 300 to 500 million people are infected worldwide. Although the past century has seen the advancement of anti-malarial compounds, a serious setback to anti-malarial programs is the high adaptability of the causative agent by mutation and it is resistant to various types of anti-malarial drugs. For this reason, new families of active anti-malarial compounds have and continue to receive significant pharmaceutical interest.

The success of the anti-malarial drug quinine and the discovery of drug artemisinin, the most potent anti-malarial drug both from plant sources have led to the study of plants as anti-malarial agent. In this context, the Applicant has recently found that use of the crude extract of *Clausena lansium* shows anti-malarial activity. However, the use of crude extract for the treatment of malaria may not be efficient and reliable. Therefore, there is a need to isolate and identify the anti-malarial active compounds present in *Clausena lansium*.

*Clausena lansium* has a high medicinal value. Its leaves, seeds, fruits and roots can be used as medicines to serve a wide variety of purposes. Various compounds from different parts of the plant have been isolated and structurally determined. Each chemical constituent is categorized according to the part of the plant from which is has been derived and its chemical class is tabulated as follows:

TABLE 1

Chemical constituents isolated from *Clausena lansium*.

| Plant Part | Chemical Class | Name of compound |
|---|---|---|
| Leaf | Amide | -(E)-N-(4-methoxyphenethyl)-2-methylbut-2-enamide |
| | | -(E)-N-2-Phenylethylcinnamamide |
| | | 9-Octadecenamide |
| | | -Clausamides I and II |
| | | -Clausenamide |
| | | -Cycloclausenamide |
| | | -Dehydrocycloclausenamide |
| | | -Homoclausenamide |
| | | -Lansamide-I |
| | | -Lansamides -2, -3, -4 |
| | | -Lansimides-1, -2, -3 |
| | | -N-2-Lansimide |
| | | -N-2-Phenylethylcinnamamide |
| | | -Neoclausenamide |
| | | -N-methylcinnamamide |
| | | -N-methyl-N-[(Z)-styryl]-3-phenyloxirane-2-carboxamide |
| | | -Secoclausenamide |
| | | -Secodemethyl-clausenamide |
| | | -z-clausenamide |
| | Carbazole alkaloid | -Heptaphylline |
| | | -Lansine |
| | Coumarin | -Anisolactone |
| | | -3-benzylcoumarin |
| | | -Clausenacoumarin |
| | | -2',3'-epoxyanisolactone |

TABLE 1-continued

Chemical constituents isolated from *Clausena lansium*.

| Plant Part | Chemical Class | Name of compound |
|---|---|---|
| | Essential oil components | Acetic acid |
| | | Acetophenone |
| | | 4'-methyl-Allaromadendrene |
| | | Benzaldehyde |
| | | Benzeneacetaldehyde |
| | | Benzoic acid |
| | | (E)-α-Bergamotene |
| | | (E)-β-Bergamotene |
| | | Bergamotol |
| | | Bicycloelemene |
| | | Bicyclogermacrene |
| | | (E)-α-Bisabolene |
| | | β-Bisabolene |
| | | (E)-γ-Bisabolene |
| | | α-Bisabolol |
| | | Borneol |
| | | Bornyl acetate |
| | | b-Santalol |
| | | Butanal |
| | | Butanoate, 2-methyl-,(3Z)-hexenyl |
| | | δ-Cadinene |
| | | Cadin-4-en-10-ol |
| | | Camphene |
| | | Camphor |
| | | n-Caproaldehyde |
| | | 3-Carene |
| | | (+)-4-Carene |
| | | (E)-Caryophyllene |
| | | Caryophyllene oxide |
| | | Copaene |
| | | Cryptone |
| | | ar-Curcumene |
| | | 1,4-Cyclohexadiene |
| | | 3-Cyclohexen-1-methanol |
| | | 2-Cyclohexen-1-one |
| | | p-Cymene |
| | | 3-Cyclohexen-1-ol |
| | | (E)-β-Damascenone |
| | | 2-Decanone |
| | | (2E)-Decenal |
| | | Denderalasin |
| | | (E)-4,8-dimethyl-1,3,7-nonatriene |
| | | Dodecane |
| | | β-Elemene |
| | | Epiglobulol |
| | | Ethanol |
| | | Ethanone |
| | | 2-Ethylfuran |
| | | Farnesal |
| | | (E,E)-Farnesal |
| | | (2E,6Z)-Farnesal |
| | | (E,E)-α-Farnesene |
| | | cis-b-Farnesene |
| | | Farnesol |
| | | β-Fenchyl alcohol |
| | | Geranyl acetate |
| | | Geranyl acetone |
| | | Golbulol |
| | | Gossonorol |
| | | Hept-5-en-2-one, 6-methyl- |
| | | 2-Hexenal |
| | | 3-Hexen-1-ol |
| | | 2-Hexenol |
| | | cis-3-Hexenyl 2-methylbutanoate |
| | | α-Humulene |
| | | Humulene epoxide II |
| | | Isosativene |
| | | (Z)-Lanceol |
| | | Ledol |
| | | Limonene |
| | | Linalool |
| | | Linolenic acid methyl ester |
| | | Longipinene |
| | | p-Mentha-1(7),8-diene |
| | | Menth-2-en-1-ol (cis-,para-) |
| | | 3-Methyl-4-brendene |

TABLE 1-continued

Chemical constituents isolated from *Clausena lansium*.

| Plant Part | Chemical Class | Name of compound |
|---|---|---|
| | | 2-Methylfuran |
| | | 6-Methyl-5-hepten-2-one |
| | | Methyl lanceol |
| | | (2E,6E)-2-methyl-6-(4-methylcyclohex-3-enylidene)hept-2-enal |
| | | Methyl santalol |
| | | Myrcene |
| | | (E)-Nerodilol |
| | | Neryl acetate |
| | | Nonanal |
| | | 2-Nonanone |
| | | (E)-β-Ocimene |
| | | (Z)-β-Ocimene |
| | | Octadec-1-ene |
| | | 1,3,6-Octatriene |
| | | Palmitic acid |
| | | 1-Pentene |
| | | cis-2-Pentenol |
| | | α-Phellandrene |
| | | β-Phellandrene |
| | | Phenylacetaldehyde |
| | | Phytol |
| | | Phytone |
| | | α-Pinene |
| | | β-Pinene |
| | | Propanal |
| | | 2-Propanone |
| | | Sabinene |
| | | (Z)-a-Santalol |
| | | Santelene |
| | | β-Santalene |
| | | Sesquiphellandrene |
| | | β-Sesquiphellandrene |
| | | Sinensal |
| | | α-Sinensal |
| | | Spathulenol |
| | | Styrene |
| | | γ-Terpinene |
| | | α-Terpineol |
| | | Terpinen-4-ol |
| | | α-Thujene |
| | | α-Thujone |
| | | Tricyclene |
| | | 2-Undecanone |
| | | Viridiflorol |
| | | Zingiberene |
| | Glycoside | Corchoionoside C |
| | | 1'-O-beta-D-glucopyranosyl (2R,3S)-3-hydroxynodakenetin |
| | | Keampferol-3-O-alpha-L-rhamnopyranosyl(1-->2) [alpha-L-rhamnopyranosyl(1-->6)]-beta- D-glucopyranoside |
| | | Mauritianin |
| | | Quercetin-3-O-robinobioside |
| | | Quercetin-3-O-scillabioside |
| | | Rutin |
| | | (6S,7E,9S)-6,9,10-trihydroxy-4,7-megastigmadien-3-one 9-O-β-d-glucopyranoside |
| | Triterpenoid | -Lansiol |
| Seed | Amide | Lansamide-I |
| | | Lansiumamides A, B, C and I |
| | | N-methyl-N-[(Z)-styryl]-3-phenyloxirane-2-carboxamide |
| | | (E)-N-2-phenylethylcinnamamide |
| | | (2'R)-N-(2'phenylethyl)-N-methylcinnamamide 2'-O-β-D-glucopyranoside |
| | | (1R), (3R)-4-methylene-1-(1-methylethyl)-(1,3)-cyclohexanediol |

TABLE 1-continued

Chemical constituents isolated from *Clausena lansium*.

| Plant Part | Chemical Class | Name of compound |
|---|---|---|
| | Polysaccharide | WP1 |
| | | WP3 |
| | Protein | *Clausena lansium* trypsin inhibitor (CLTI) |
| | Essential oil components | Acetic acid |
| | | Allaromadendrene |
| | | (+)-Aromadendrene |
| | | Benzaldehyde |
| | | Benzeneacetaldehyde |
| | | Benzoic acid |
| | | Bergamotol |
| | | Bicyclogermacrene |
| | | Bornyl acetate |
| | | Butanal |
| | | Cadina-1(10),4-diene |
| | | Cadinene |
| | | Camphene |
| | | Carene |
| | | (+) 4-Carene |
| | | 3-Carene |
| | | Caryophyllene |
| | | ar-Curcumene |
| | | 1,4-Cyclohexadiene |
| | | 3-Cyclohexen-1-methanol |
| | | 3-Cyclohexen-1-ol |
| | | 2-Cyclohexen-1-one |
| | | Copaene |
| | | Cyclohexene |
| | | Cymene |
| | | (E)-4,8-dimethyl-1,3,7-nonatriene |
| | | Ethanol |
| | | Ethanone |
| | | 2-Ethylfuran |
| | | Geranyl acetate |
| | | Germacrene D |
| | | Hexanal |
| | | 2-Hexenal |
| | | 3-Hexen-1-ol |
| | | cis-3-Hexenyl 2-methylbutanoate |
| | | Isosativene |
| | | Limonene |
| | | Linalool |
| | | p-Menth-1-en-4-ol |
| | | 3-Methyl-4-brendene |
| | | 6-Methyl-5-hepten-2-one |
| | | 2-Methylfuran |
| | | Methyl isopropenyl-cyclohexen-1-ol |
| | | Myrcene |
| | | Nerol acetate |
| | | 2-Nonanone |
| | | 1,3,6-Octatriene |
| | | 1-Pentene |
| | | cis-2-Pentenol |
| | | Phellandrene |
| | | 2-Propanone |
| | | Propanal |
| | | Sabinene |
| | | Santalene |
| | | Styrene |
| | | Terpinen |
| | | Terpineol |
| | | Thujene |
| | | trans-b-Ocimene |
| | | Tricyclene |
| | | α-Bergamotene |
| | | α-Farnesene |
| | | α-Humulene |
| | | α-Phellandrene |
| | | α-Pinene |
| | | α-Santalol |
| | | α-Thujene |
| | | α-Zingiberene |
| | | β-Bisabolene |
| | | β-Caryophyllene |
| | | β-Fenchyl alcohol |
| | | β-Pinene |
| | | β-Santalene |

TABLE 1-continued

Chemical constituents isolated from *Clausena lansium*.

| Plant Part | Chemical Class | Name of compound |
|---|---|---|
| | | β-Santalol |
| | | β-Sesquiphellandrene |
| | | γ-Terpinene |
| | | δ-Cadinene |
| Stem/branch/twig | Amide | Dihydroalatamide |
| | | N-Phenethylcinnamide |
| | | N-(Phenethyl)benzamide |
| | | Tembamide |
| | Carbazole alkaloid | Claulamines A and B |
| | | Claulansines A - J |
| | | Claulansine L - R |
| | | Claulansine S - T |
| | | Clausenaline A |
| | | Clausines D and I |
| | | Daurine |
| | | 3-Formyl-6-methoxycarbazole |
| | | 3-Formylcarbazole |
| | | Glycozolidal |
| | | Indizoline |
| | | Mafaicheenamine A |
| | | Methyl-6-methyoxycarbazole-3-carboxylate |
| | | 3-Methylcarbazole |
| | | 6-Methoxyheptaphylline |
| | | 2-Methoxy-1-(3-methyl-buten-1-yl)-9H-carbazole-3-carbaldehyde |
| | | Methylcarbazole-3-carboxylate |
| | | Murrayanine |
| | | Phenethyl cinnamide |
| | Coumarin | Claucoumarins A-D |
| | | Clausenalansimin A and B |
| | | Heraclenin |
| | | Heraclenol |
| | | Xanthotoxol |
| | | Imperatorin |
| | | Isogospherol |
| | | Isoheraclenin |
| | | Isoimperatorin |
| | | Indicolactonediol |
| | | Isoscopoletin |
| | | Lansiumarins A, B, C |
| | | 5-{[(E)-3-methyl-4-((2S,4R)-4-methyl-5-oxotetrahydrofuran-2-yl)but-2-en-1-yl]oxy}-psoralen |
| | | 8-geranoxypsoralen |
| | | 9-[3-methyl-4-(4-methyl-5-oxo-tetrapydrofuran-2-yl)but-2-enyloxy]-furo[3,2-g]chromen-7-one |
| | | Osthol |
| | | Wampetin |
| | Glycoside | Clausenosides A and B |
| | | Isotachioside |
| | | Methyl salicylate d-glucoside |
| | | Xanthotoxol 8-O-b-d-glucopyranoside |
| | Quinolone alkaloid | 4-methoxy-N-methyl-2-quinolone |
| | Sesquiter-penoid | Oplopanone |
| | Steroid | -β-sitosterol |
| | | -Stigmast-4-en-3-one |
| | | -Stigmast-4-en-6β-ol-3-one |
| | | -5α-stigmastan-3-one |
| | Triterpenoid | -α-amyrin |
| | | -Lupeol |
| Stem bark | Coumarin | -3-formylcarbazole |
| | | -Chalepin |
| | | -Imperatorin |
| | | -Phellopterin |
| Stem and root | Amide | Claulansamides A and B |
| | | (−)-clausenamide |
| | | Clausenalansamides A and B |
| | | (−)-(R)-tembamide |
| | Quinolone | Atanine |
| | | Dictamine |
| | | 6-hydroxy-4-methoxy-1-methyl-2-quinolone |
| | | 6-hydroxy-4-methoxy-1-methyl-2-quinolone |

TABLE 1-continued

Chemical constituents isolated from *Clausena lansium*.

| Plant Part | Chemical Class | Name of compound |
|---|---|---|
| Root | Amide | 4-methoxy-1-methyl-2-quinolone<br>(β)-(S)-platydesmine<br>Angustifoline |
| | Carbazole alkaloid | Claulamines C, D, E<br>Clausenalines B-F<br>O-demethylmurrayanine<br>2,7-dihydroxy-3-formyl-<br>1-(3'-methyl-2'-butenyl)carbazole<br>3-Formylcarbazole<br>3-Formyl-6-methoxycarbazole<br>3-Formyl-1,6-dimethoxycarbazole<br>Glycozoline<br>Glycozolidal<br>Glycolidizal<br>Imperatorin<br>Indicolactonediol<br>Indizoline<br>Lansine<br>Mafaicheenamines B, D and E<br>Methyl 6-methoxycarbazole-3-<br>carboxylate<br>Methyl carbazole-3-carboxylate<br>Murrayanine<br>Umbelliferone<br>Wampetin |
| | Coumarin | -Chalepensin<br>-Chalepin<br>-Clausemarins A-D<br>-Gravelliferone |
| | Steroid | Sitosterol |
| Fruit | Coumarin | Anisolactone<br>3-Benzyl-2H-chromen-2-one<br>Clauslactone V<br>Clauslactone W<br>Clausenalansimin B<br>8-Hydroxypsoralen<br>Indicolactone<br>Wampetin<br>Xanthotoxol |
| | Carbazole alkaloid | Carbazole-3-carboxylic acid<br>Claulansine J<br>Claulansine K<br>O-demethylmurrayanine<br>Methyl-8-hydroxycarbazole-3-carboxylate<br>Methylcarbazole-3-carboxylate<br>Mukonal |
| | Jasmonoid glucoside | 12-β-d-glucopyranosyloxy-6-epi-7-<br>isocucurbic acid-1,6-lactone<br>12-β-d-glucopyranosyloxyjasmonic acid<br>12-hydroxyjasmonic acid |
| | Sesquiterpene | (+)-curcumen-12-oic acid<br>(+)-(E)-α-santalen-12-oic acid |
| | Essential oil components | Acetic acid<br>Allaromadendrene<br>(+)-Aromadendrene<br>Benzaldehyde<br>Benzeneacetaldehyde<br>Benzoic acid<br>Bergamotene<br>α-Bergamotene<br>Bicyclogermacrene<br>β-Bisabolene<br>Borneol<br>Bornyl acetate<br>Butanal<br>δ Cadinene<br>cis-Calamenene<br>Camphene<br>α-Campholenealdehyde<br>3-Carene<br>(+)4-Carene<br>Carvota acetone<br>β-Caryophllene<br>Caryophyllene oxide<br>Copaene<br>ar-Curcumene |

TABLE 1-continued

Chemical constituents isolated from *Clausena lansium*.

| Plant Part | Chemical Class | Name of compound |
|---|---|---|
| | | γ-Curcumene |
| | | 1,4-Cyclohexadiene |
| | | Cyclohexene |
| | | 3-Cyclohexen-1-methanol |
| | | 3-Cyclohexen-1-ol |
| | | 2-Cyclohexen-1-one |
| | | (E)-4,8-dimethyl-1,3,7-nonatriene |
| | | Ethanol |
| | | Ethanone |
| | | 2-Ethylfuran |
| | | α-Farnesene |
| | | trans-β-Farnesene |
| | | Farnesol |
| | | α-Fenchene |
| | | β-Fenchene |
| | | Fenchol |
| | | β-Fenchyl alcohol |
| | | Geranyl acetate |
| | | Hexadecanoic acid |
| | | Hexanal |
| | | 2-Hexenal |
| | | 3-Hexen-1-ol |
| | | cis-3-Hexenyl 2-methylbutanoate |
| | | α-Humulene |
| | | Isoborneol |
| | | Isosativene |
| | | Limonene |
| | | δ-Limonene |
| | | cis-Limonene oxide |
| | | Limonyl alcohol |
| | | Linalool |
| | | cis-Linalool oxide |
| | | p-Menth-1-en-4-ol |
| | | p-Menth-1-en-8-ol |
| | | p-Menth-2-en-1-ol |
| | | 1H-3a,7-methanoazulene |
| | | 3-Methyl-4-brendene |
| | | 2-Methylfuran |
| | | 6-Methyl-5-hepten-2-one |
| | | α-Muurolene |
| | | Myrcene |
| | | Naphthalene |
| | | Nerolidol |
| | | 2-Nonanone |
| | | trans-β-Ocimene |
| | | 1-Octanol |
| | | 1,3,6-Octatriene |
| | | 1-Pentanol |
| | | 1-Pentene |
| | | cis-2-Pentenol |
| | | Phellandral |
| | | Phellandrene |
| | | α-Phellandrene |
| | | β-Phellandrene |
| | | Phellandrene epoxide |
| | | Phytol |
| | | β-Pinene |
| | | α-Pinene |
| | | α-Pinene oxide |
| | | Piperitone |
| | | Propanal |
| | | 2-Propanone |
| | | Pulegone |
| | | Sabinene |
| | | β-Santalene |
| | | Santalol |
| | | α-Santalol |
| | | β-Santalol |
| | | β-Sesquiphellandrene |
| | | Sinensal |
| | | Spathulenol |
| | | Stearic acid |
| | | Styrene |
| | | γ-Terpinene |
| | | δ-Terpineol |
| | | α-Thujene |

TABLE 1-continued

Chemical constituents isolated from *Clausena lansium*.

| Plant Part | Chemical Class | Name of compound |
|---|---|---|
| | | Tricyclene |
| | | Valencene |
| | | α-Zingiberene |
| Flower | Amide | 9-Octadecenamide |
| | | (E)-N-2-phenylethylcinnamamide |
| | Essential oil components | Acetophenone |
| | | Bergamotol |
| | | Butyl octanol |
| | | Cadinol |
| | | β-Caryophyllene |
| | | Caryophyllene |
| | | Caryophyllene oxide |
| | | Denderalasin |
| | | n-Dodecane |
| | | Farnesene |
| | | Hexadecanoic acid |
| | | Lanceol |
| | | Ledol |
| | | Linalool |
| | | p-Menth-1-en-4-ol |
| | | p-Menth-1-en-8-ol |
| | | Nerolidol |
| | | Octadecadienoic acid |
| | | Palmitamide |
| | | n-Pentadecane |
| | | α-Santalol |
| | | β-Santalol |
| | | Sinensal |
| | | Spathulenol |
| | | Stearamide |

An aspect of the present invention is to provide a method of treating and/or preventing a parasitic mediated disease in a subject, comprising administering to the subject a therapeutically effective amount of a pharmaceutical composition comprising a furanocoumarin derivative, its pharmaceutical acceptable salt, isomer or a combination thereof.

The inventors have found that compound anisolactone (isolated from a plant) which had previously been shown to demonstrate hypoglycaemic activity, exhibits a good antimalarial activity.

The terms "treat, treatment and treating", as used herein refer to reducing or lessening the symptoms of the parasitic mediated disease in a subject.

The term "preventing" as used herein refers to blocking or reducing the possibility of contracting the parasitic mediated disease in a subject for example by reducing or lessening the symptoms of the parasitic mediated disease in a subject upon contact with a parasite of the disease by administering the compound to the subject prior to any infection. In various embodiments, the prevention takes place via direct inhibitory action of the therapeutically effective amount of a pharmaceutical composition on parasite. In various embodiments, the therapeutically effective amount of a pharmaceutical composition is administered to a healthy subject at risk of coming into contact with a parasite. In various embodiments, the therapeutically effective amount of a pharmaceutical composition is administered to a healthy subject at least 48 hours before the subject is in an environment where the parasitic disease may be contracted.

The term parasitic mediated disease as used herein refers to any disease that is caused by a parasite and results in unwanted symptoms in a subject. The disease may include malaria, leishmanial, dengue, chargas disease, Lyme disease, *giardia* as well as other diseases known in the art. In various embodiments, the parasitic mediated disease is malaria.

In various embodiments the parasite is an indirect parasite transmitted by a vector to the subject. In various embodiments, the parasitic mediated disease is transmitted by an arthropod. As used herein, the term "arthropod" refers to an invertebrate animal having an exoskeleton and a segmented body. The arthropod vector may include any haematophagous arthropod that may include mosquitoes, flies, sand flies, lice, fleas, ticks or mites. In various embodiments the arthropod comprises a mosquitoes from the *Culex, Anopheles, Culseta, Mansonia* or *Aedes* genus. In various embodiments, the arthropod comprises an *Anopheles* genus.

In various embodiments the indirect parasite may be an endo-parasite including helminths, protozoa, bacteria or viruses. In various embodiments the parasite is an intercellular parasite that may include protozoa, bacteria or viruses. In various embodiments the intercellular parasite is a protozoa such as a *Plasmodium* species, *Entamoeba* species, *Giardia* species, *Trypanosoma* species or any other protozoa known in the art to cause parasitic disease. In various embodiments, the parasitic mediated disease is caused by a *Plasmodium* parasite. The *Plasmodium* parasite may be any *Plasmodium* species known in the art to cause parasitic disease including *P. falciparum, P. vivax, P. knowlesi, P. malariae, P. reichenowi, P. ovale* or *P. falciparum* 3D7 (a chloroquine-sensitive strain).

In various embodiments, the route of administration is oral, intravenous, sublingual, subcutaneous, intramuscular or any other route of administration known in the art.

The term "subject" as used herein refers to an animal. In various embodiments the subject may include birds, rodents, reptiles or primates. In various embodiments, the subject is a human.

The term "therapeutically effective amount" as used herein refers to an amount of the pharmaceutical compound that is able to reduce or lessen the symptoms of the parasitic mediated disease in a subject. A person skilled in the art would be able to calculate a therapeutically effective amount based on a subject weight and size to ensure that the amount is above the $IC_{50}$ of the compound when administered to a subject.

In various embodiments, the furanocoumarin derivative comprises a linear furanocoumarin core having the following core structure (A).

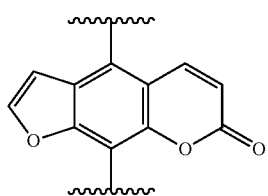

(A)

In various embodiments, the furanocoumarin derivative has the following structure (1a):

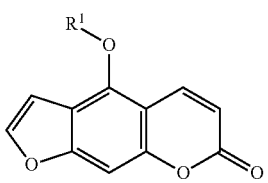

(1a)

wherein $R^1$ is an aliphatic chain comprising a cyclic ester functional group.

In various embodiments, the furanocoumarin derivative has the following structure (2a):

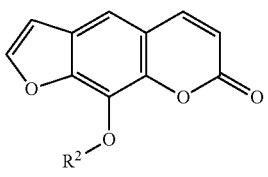

(2a)

wherein $R^2$ is an aliphatic chain comprising a cyclic ester functional group.

In various embodiments, the aliphatic chain comprises an unsaturated moiety. In various embodiments, the unsaturated moiety comprises a double bond.

In various embodiments, the cyclic ester functional group comprises a 5-membered ring cyclic ester functional group. In various embodiments, the cyclic ester functional group comprises a furanonyl group.

In various embodiments, the furanocoumarin derivative comprises a furanocoumarin core with a sidechain comprising methylfuranone.

In various embodiments, the furanocoumarin derivative comprises anisolactone having the following structure (1b):

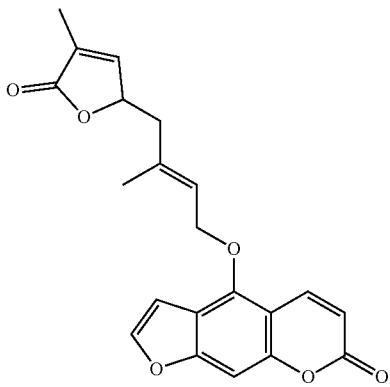

(1b)

In various embodiments, the furanocoumarin derivative comprises wampetin having the following structure (2b):

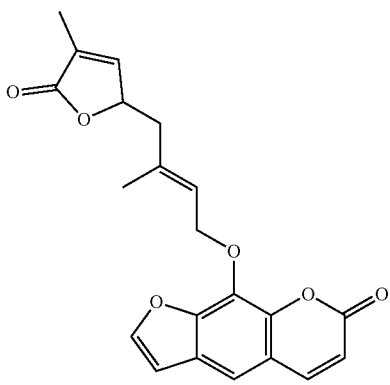

(2b)

In various embodiments, the furanocoumarin derivative comprises indicolactone having the following structure (2c):

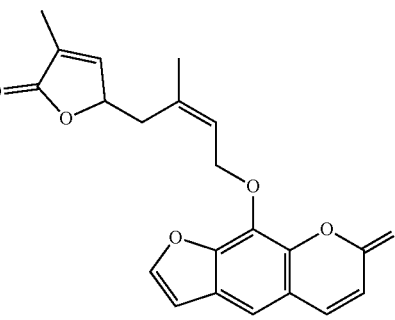

(2c)

In various embodiments, the furanocoumarin derivative is isolated from a plant. In various embodiments, the plant comprises a member of the Rutaceae family. In various embodiments, the plant comprises a *Clausena lansium* species. In various embodiments, the furanocoumarin derivative is isolated from the leaves of the plant.

As used herein, the term "*Clausena lansium*" is synonymous with *Clausena wampi* (Blanco) Oliv.; *Clausena punctate* (Sonn.) Rehder & E. H. Wils.; *Cookia punctate* Sonn; *Cookia wampi* Blanco; *Quinaria lansium* Lour.; *Aulacia*

*punctate* (Sonn.) Raeusch; and *Sonneratia punctata* (Sonn.) J. F. Gmel and *Clausena lansium* (Lour.) Skeels.

Depending on the country, the plant *Clausena lansium* is given vernacular names and most of them are derived from its Chinese name: huang-pi-kuo, huang-pi-he, huang-pi-kan, or huang-pi-tzu. In Malaysia, it is known as wampee, wampoi, or wang-pei, in Thailand, som-ma-fai or mafai jeen; in the Philippines, uampi, uampit, huampit or galumpi; in Vietnam, hong bi, or hoang bi; in Cambodia, kantrop; in Laos, somz mafai; in Sri Lanka and other countries, Fool's curry leaf.

Another aspect of the present invention provides a compound for use in the treatment and/or prevention of a parasitic mediated disease, the compound comprises a furanocoumarin derivative its pharmaceutical acceptable salt, isomer or a combination thereof.

Terms mentioned in the compound for use are defined in a similar manner as the like terms mentioned above.

Another aspect of the present invention provides a method of manufacturing a compound comprising a furanocoumarin derivative or its pharmaceutical acceptable salt, isomer or a combination thereof for the treatment and/or prevention of a parasitic mediated disease.

In various embodiments the compound can be manufactured synthetically. In various other embodiments the compound is manufactured by a method of isolating the compound from the leaves of a *Clausena lansium* plant as outlined below.

Other terms mentioned in the method of manufacture are defined in a similar manner as the like terms mentioned above.

Another aspect of the present invention provides a method of isolating a compound from the leaves of plant *Clausena lansium* comprising the step of macerating the leaves in a solvent, wherein the compound comprises a furanocoumarin derivative having core structure (A):

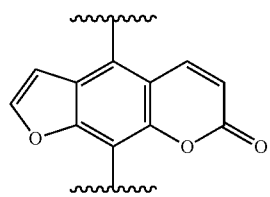

(A)

In various embodiments, the method of isolating a compound from the leaves of plant *Clausena lansium*, further comprising the step of evaporating the solvent to afford a maceration extract.

In various embodiments, the method of isolating a compound from the leaves of plant *Clausena lansium*, further comprising the steps of:
(a) defatting leaves of a plant comprising *Clausena lansium*,
(b) macerating the defatted leaves in a solvent to form a first extract,
(c) acidifying the first extract to form an acidified extract,
(d) filtering the acidified extract to obtain a filtrate,
(e) basifying the filtrate to form a basified filtrate,
(f) extracting the basified filtrate with dichloromethane to form a second extract,
(g) separating the second extract into a first aqueous fraction and second dichloromethane fractions.
(h) drying the first and second fractions, wherein the compound comprises a furanocoumarin derivative or its isomers present in the first and/or second fraction.

The term defatting as used herein refers to removal of fat. In various embodiments the defatting step comprises removing fats, chemically or physically or by a combination of chemical and physical means known in the art. In various embodiments, the defatting comprises ultrasonication in a hydrocarbon solvent. In various embodiments, the hydrocarbon is hexane.

In various embodiments, the solvent is a polar solvent. In various embodiments, the polar solvent is an alcohol solvent. In various embodiments, the alcohol solvent is ethanol.

In various embodiments, the dichloromethane fraction is further extracted with an alcohol solvent. In various embodiments, the alcohol solvent is butanol.

In various embodiments, the acidifying step comprises adding a strong acid having a pKa of 2 or below. In various embodiments, the acidifying step comprises adding hydrochloric acid solution. In various embodiments, the concentration of the hydrochloric acid solution is about 1N. In various embodiments, the basifying step comprises adding a strong alkali having a pKa of 20 or above. In various embodiments, the basifying comprises adding sodium hydroxide solution. Preferably, the concentration of the sodium hydroxide solution is about 1N.

In various embodiments, the second dichloromethane fraction is separated by column chromatography.

In various embodiments, the first extract is dissolved in ethanol prior to acidifying.

In various embodiments one or more step may be repeated to increase purity and/or yield.

Other terms mentioned in the method of isolation are defined in a similar manner as the like terms mentioned above.

In various embodiments, the term "maceration" refers to softening and breaking down of a solid by soaking the solid in a solvent. In various embodiments, the organic solvent is an alcoholic solvent. In various embodiments, the alcoholic solvent is ethanol. In various embodiments, the step of macerating the leaves is conducted at room temperature. In various embodiments, fresh organic solvent is replaced every 24 hours.

It should be further appreciated by the person skilled in the art that variations and combinations of features described above, not being alternatives or substitutes, may be combined to form yet further embodiments falling within the intended scope of the invention.

Examples of Preferred Embodiments

A. General Remarks

For extraction, column chromatography and thin layer chromatography (TLC), all chemicals used were analytical (ACS) grade. Chemical analyses by gas-chromatography-mass spectrometry (GC-MS) and high performance liquid chromatography (HLPC) were carried out using HPLC grade solvents. For the latter, milli-Q water (Direct-Q 3, Millipore, France) was also used. The following chemicals were purchased from Tedia Company Inc. (Fairfield, Ohio, USA): acetone (ACS), acetonitrile (HPLC), 95% ethanol (ACS), 95% n-hexane (ACS), dichloromethane (ACS), methanol (ACS, HPLC). Butanol (ACS) was purchased from Thermo Fisher Scientific Inc. (Waltham, Massachusetts, USA). Nuclear Magnetic Resonance (NMR) spectroscopy was carried out using deuterated chloroform from Sigma-Aldrich (St. Louis, Missouri, USA). 1 N Hydrochloric acid and 1 N sodium hydroxide were purchased from Merck (Damstadt, Germany). Commercial standards for artesunate, chloroquine diphosphate and isoimperatorin were purchased from Sigma-Aldrich (St. Louis, Missouri, USA). Thin layer chromatography (TLC) was carried out using aluminium sheets coated with silica gel 60 F254 TLC sheets from Merck (Damstadt, Germany). Kieselgel 60 (0.063-0.200 mm, 70-230 mesh) silica gel from Merck (Damstadt, Germany) was used for packing of columns for column chromatography.

B. Isolation of the Compounds

Fresh leaves of Plant *Clausena lansium* were collected in August 2014. The collected plant parts were washed with water, dried manually by wiping the surfaces with tissue, and blended using Morries kitchen blenders before extraction. Unless otherwise stated, all leaves were extracted fresh.

Alkaloidal extraction: The collected fresh leaves were blended using a kitchen blender to give 2.95 kg of fresh plant material, which was further defatted by ultrasonicating in 95% hexane for 30 minutes for 3 cycles. Fresh hexane was used for each cycle. After each cycle, the extract was decanted and collected. The remaining plant material after defatting was subjected to maceration in 95% ethanol for 3 days in the dark at room temperature, with occasional agitation to increase the efficiency of maceration. The menstruum was collected and dried using a rotary evaporator. The dried extract was then redissolved in a minimal volume of ethanol. 500 ml of 1 N hydrochloric acid was added to the extract to pH 2 while on ice for 3 hours, and then kept in the refrigerator overnight, and filtered the next day. 400 ml of 1 N hydrochloric acid was further added to the filtrate, which was then kept overnight in the refrigerator and filtered the next day. The total filtrate collected was basified with 1 N sodium hydroxide to pH 10 while on ice. The basified extract was then subjected to liquid-liquid extraction (LLE) with one-third the volume of dichloromethane (DCM). The LLE was repeated twice, replacing with fresh DCM each time. Thereafter, another LLE was done with the DCM fraction using butanol at the same volume ration and repeated twice. All fractions obtained from LLE, namely the aqueous, DCM, and butanol fractions were dried and kept separately.

Ethanolic maceration: Fresh leaves were macerated in 650 ml of 95% ethanol for three days at room temperature, with occasional agitation to increase the efficiency of maceration. Fresh solvent was replaced after every 24 hours. The solvent was then evaporated off using a rotary evaporator to afford a crude ethanolic maceration extract.

For sample preparation for chemical analyses, the dried extracts, fractions, subfractions, and isolated compounds were dissolved in methanol, and the solution filtered through a 0.45 μm filter before sample injection. Crude plant extracts, fractions, and subfractions were prepared at concentrations of 5 mg/ml for high performance liquid chromatography (HPLC) and gas chromatography-mass spectrometry (GC-MS) analyses, and 1 mg/ml for liquid chromatography-mass spectrometry (LC-MS) analysis. Standards and the isolated compound were prepared at 1 mg/ml for HPLC and GC-MS analyses, and 0.1 mg/ml for LC-MS analysis.

C. Column Chromatography of Dichloromethane Fraction

Silica gel of varying mesh sizes (0.063-0.200 mm, 0.04-0.063 mm and 0.015-0.040 mm) (Merck, Damstadt, Germany) was used as the stationary phase for packing of columns for column chromatography. Silica gel was made into slurry by mixing with hexane and loaded onto the column with frequent tapping of the column to remove trapped air bubbles and increase efficiency of column packing. Samples were loaded onto the column by dry loading. The sample to be separated by column chromatography was reconstituted in a minimal volume of solvent in which it was completely soluble. Silica gel was activated by heating at 120° C. for 1 hour. This activated silica gel was used to adsorb the reconstituted sample, and allowed to completely dry (i.e. until it appears as finely flowing powder with no clumps). The sample was then loaded on the column as a thin band. Fractions were eluted from the column using varying concentrations of two-solvent mixtures (i.e. hexane-dichloromethane, dichloromethane-methanol) in increasing polarity. The elution of fractions was monitored using TLC.

TLC was carried out using aluminium sheets coated with silica gel 60 F254 (Merck, Darmstadt, Germany) as the stationary phase and varying concentrations of binary solvent systems (combinations of hexane, dichloromethane, methanol) as the mobile phase. Spots on TLC plates were detected under ultraviolet (UV) light (Spectroline ENF-240C/FE, Spectronics Corporation, Westbury, USA) at wavelengths of 254 and 365 nm, as well as derivatized by spraying with vanillin reagent and heating at 120° C. Vanillin reagent was prepared using 45 ml ethanol, 45 ml water, 1 g vanillin and 10 ml concentrated sulphuric acid.

Dichloromethane (DCM) fraction (1.4 g) was separated on a silica gel column chromatography with an internal diameter of 2 cm. The sample bed length was 2.2 cm, and the column bed length was 17 cm. Elution was carried out using gradients of hexane-DCM (100% hexane to 200% DCM), followed by DCM-methanol (100% DCM to 100% methanol), yielding 25 subfractions. Compounds on TLC plates were detected under ultraviolet (UV) light at wavelengths of 254 and 365 nm, as well as by spraying with vanillin reagent. Fractions with similar TLC profiles were pooled.

The crude ethanolic maceration extract (110 g) was separated on a silica gel column with an internal diameter of 7 cm. The sample bed length was 9 cm, and the column bed length was 22 cm. Fractions were eluted in the same manner as described above.

D. Characterization of the Compounds/Chemical Analysis

For sample preparation for chemical analyses, the dried extracts, fractions, subfractions, and isolated compounds were dissolved in methanol, and the solution filtered through a 0.45 μm filter (Filtrex, Agilebt, USA) before sample injection. Concentrations of 5 mg/ml were prepared for crude extracts and fractions, 1 mg/ml for subfractions and 0.1 mg/ml for standard compounds for HPLC and GC-MS analyses. Concentrations of 0.1 mg/ml for crude extracts, 10 μg/ml for fractions and 1 μg/ml for standards were prepared for LC-MS analyses.

D.1 High Performance Liquid Chromatography-Diode Array Detected (HPLC-DAD)

An Agilent 1260 Infinity series HPLC-DAD equipped with a quaternary gradient pump was used for qualitative analyses. Data was acquired and processed using ChemStation for LC 3D Systems (Agilent Technologies, USA). The mobile phases used were (A) Milli-Q water and (B) acetonitrile. Analyses of crude extracts and isolated compounds were carried out using a Zorbax Eclipse XDB-C18 revered-phase column (5 μm, 250 mm×4.6 mm i.d.; Agilent Technologies, USA). The flow rate of the mobile phase was 1 ml/min. Injection volume was 5 μl. The UV and visible spectra from 210-300 nm were recorded online during the chromatographic run. Table 2 below shows the gradient elution profile used for analyses of isolated compounds.

TABLE 2

Gradient elution profile used for analyses of isolated compounds

| Time (min) | % Water | % Acetonitrile |
|---|---|---|
| 0 | 95 | 5 |
| 15 | 85 | 15 |
| 35 | 50 | 50 |
| 60 | 10 | 90 |
| 65 | 0 | 100 |
| 70 | 0 | 100 |

D.2 Gas Chromatography-Mass Spectrometry (GC-MS)

GC-MS analysis was carried out using a Shimadzu GC-MS-QP 2010 (Shimadzu, Japan) fitted with a DB-5MS column (30 m×0.25 mm×0.25 μm; Agilent Technologies, USA), in electron impact ionization mode. GC operating parameters used were—injection mode: splitless, injection temperature: 250° C., carrier gas: helium at 0.95 ml/min. The column oven temperature was increased from 60-80° C. at a rate of 5° C. per min, then increased from 80-200° C. at the same rate, followed by an increase from 200-250° C. at 8° C. per min, and from 250-300° C. at 10° C. per min, with a total programme time of 57.25 mins. MS parameters used were: electron impact ionization mode, ion source temperature: 200° C. Mass spectral identification of compounds was carried out by comparing mass spectra data with those of authentic reference standards in the National Institute of Standards and Technology (NIST, USA) and WILEY Registry of Mass Spectral Data ($7^{th}$ edition) (Wiley, New York) mass spectral libraries. Qualitative analyses of compounds were carried out by comparing the retention times and mass spectra of compounds identified in the samples with those of authentic reference standards if available.

D.3 High Resolution Electrospray Ionization Mass Spectrometry (HREIMS)

The isolated compound was dissolved in methanol at a concentration of 10 ppm. The solution was injected into the LTQ Orbitrap XL™ hybrid FTMS system (Thermo Fischer Scientific, Bremen, Germany) controlled by the Xcalibur software version 2.0.7). The electrospray ionization (ESI) source was operated in the positive ion mode with spray voltage set at 3 kV, sheath gas flow rate at 60 arb, auxiliary gas flow rate at 10 arb, capillary voltage and temperature at 30 V and 275° C., respectively. The tube lens were set at 90 V, mass range was set from 75 to 700 Da with a resolution of 30,000. The accurate mass interpretation was performed using the Mass Frontier software (version 5.0).

D.4 Nuclear Magnetic Resonance (NMR) Spectroscopy $^1H$ and $^{13}C$ NMR spectra of the isolated compound were recorded on a Bruker Avance DRX 400 NMR spectrometer at 400 MHz ($^1H$) and at 100 MHz ($^{13}C$). Chemical shifts are given in ppm relative to tetramethylsilane using the residual $CHCl_3$ peak in $CDCl_3$ solution as the internal standard (7.26 ppm and 77.36 ppm respectively).

D.5 Fourier Transform Infrared Spectroscopy (FT-IR)

FT-IR spectra of the isolated compound were measured on attenuated total reflection (ATR) on a Spectrum 100 FT-IR spectrometer from Perkin Elmer (Waltham, Massachusetts, USA) and recorded over the spectral range of 4000-650 $cm^{-1}$.

Melting Point Determination

Melting point determination was performed on a Gallenkamp melting point apparatus.

E. Blood Collection and Parasites

For malaria culture, venous blood (not more than 50 ml) was collected by venepuncture from healthy adult volunteers. Host leukocytes were removed using a CF11 column, and packed infected red blood cells were used for the in vitro drug sensitivity assay. Ethical approval for this study was obtained from the Institutional Review Board, National University of Singapore (IRB protocol reference: B-14-056).

F. *Plasmodium falciparum* Culture, Synchronization and Cryopreservation

Parasites were thawed and grown in leukocyte-depleted red blood cells at 2% haematocrit at 37° C. in controlled conditions (3% oxygen, 4% carbon dioxide and 93% nitrogen), in RPMI 1640 tissue culture medium supplemented with 50 μg/ml hypoxanthine, 25 mM 4-(2-hydroxyethyl) piperazine-1-ethanesulfonic acid (HEPES), 0.3 g/L L-glutamine, 11 mM glucose, 25 mM $NaHCO_3$, 2.5 μg/ml gentamicin and 0.5% w/v Albumax II.

Parasites were synchronized using sorbitol treatment. Red blood cells were resuspended in 5% (w/v) D-sorbitol and incubated at 37° C. for 20 minutes, after which the erythrocytes were washed twice, resuspended in RPMI and returned to culture conditions. Thin smears were made before and after each experiment to determine parasitemia and parasite stage.

The ring stages of *Plasmodium falciparum* were cryopreserved according to an adapted method from Kosaisavee et al. (2006). The culture was centrifuged at 2000 rpm for 5 minutes and supernatant removed. Glycerolyte was drawn up using a syringe to a volume equivalent to 33% of the cell pellet volume and added to the pellet dropwise with continuous agitation of the tube to mix the contents. The suspension was incubated for 5 minutes at room temperature before adding the rest of the glycerolyte in the same dropwise manner. The red blood cell-glycerolyte mixture was then aliquoted into cryovials and frozen at −80° C. overnight before being stored in liquid nitrogen.

G. In Vitro Drug Sensitivity Assay

Anti-malarial activity was tested against *Plasmodium falciparum* 3D7 (chloroquine-sensitive strain) and Dd2 (chloroquine-resistant strain) using a protocol modified from the World Health Organization (WHO) microtest.

Crude extracts or fractions were preliminarily screened at a single concentration. For preliminary screening of isolated compounds, the starting concentrations used were 11.36 μg/ml and 5.953 μg/ml. Duplicates were performed. Samples which showed total growth inhibition at the end of the incubation period were then further screened to determine their $IC_{50}$. Seven concentrations of serial dilutions (two-fold) of each extract were added in duplicate on the 96-well pre-dosed drug plates (Nunc, Singapore). In both cases, artesunate and chloroquine were used as the positive controls, with maximum concentrations of 19 ng/ml and 308.7 ng/ml respectively. Triplicates were performed for $IC_{50}$ determination.

200 μl of a 2% haematocrit blood medium mixture consisting of RPMI 1640, 40 mg/ml gentamicin sulphate, 25 mM PEPES, 11 mM glucose, 200 µM hypoxanthine, and 0.5% w/v Albumax II (Gibco, Singapore) was added to each well of plates pre-dosed with the extracts. The parasites were cultured continuously in vented culture flasks in a gas chamber at 37° C. with 5% $CO_2$ until they reached mature stage. Incubation was stopped and the plates were harvested when 85% of ring stage parasites had reached the mature schizont stage in the drug-free control.

Thick blood smears were made from each well and stained with 5% Giemsa solution for 15 mins, and examined microscopically. The average number of schizonts (defined as parasites with five or more chromatin dots visible under microscopy) remaining at the end of the 42-48 hour incubation period per 100 parasites in each well was determined by microscopy, and normalized to the control well. Ring stage parasites and gametocytes were not included in the count. The dose-response curves were analysed using non-linear regression analysis, and the concentration which inhibited 50% growth ($IC_{50}$) was derived using an inhibitory sigmoid $E_{max}$ model (Le Nagard et al. 2011).

Anti-malarial screening results showed that Compound 1 is active against *Plasmodium falciparum* 3D7 with an $IC_{50}$ of 7.50 µg/ml (or 20.5 µM) (n=3).

H. Cytotoxicity Assay

Active extracts or fractions, isolated compounds and chloroquine were prepared at concentrations of 1 mg/ml while artesunate was prepared at a concentration of 0.067 mg/ml. Serial dilutions were performed using complete media (RPMI supplemented with 10% foetal bovine serum). The final concentration of DMSO for all test samples was not more than 0.4%.

Cytotoxicity was determined using the WST-1 assay (WST-1 cell proliferation reagent, Roche, Singapore). Exponentially growing NL20 cells were plated in 96-well plates at an optimized cell density of $3.5 \times 10^4$ cells/100 µl. The adherent cells were incubated overnight at 37° C. and 5% $CO_2$ to allow attachment. After 48 h of treatment with test samples, the media were aspirated and replaced with 10% v/v WST-1 in complete media. The plates were incubated for 30 min. The absorbance in each well was quantitated at 440 nm against a reference wavelength of 650 nm using a microplate reader (EnSpire Multimode Plate Reader, PerkinElmer, USA).

Cell viability was expressed as a percentage of the vehicle control. Positive controls were artesunate and chloroquine. The $CC_{50}$ values (50% cytotoxicity concentration) were determined using GraphPad Prism 6 (GraphPad Software, Inc., USA). Each reported value is the mean±SD from three independent experiments. The selectivity index (SI) was determined by taking the ratio of $IC_{50}$ against *P. falciparum* and $CC_{50}$ against NL20 cells.

I. Haemolysis Assay

The toxicity of anisolactone in uninfected host RBCs was evaluated using the haemolysis assay, according to a protocol described previously by Sarkar et al. (2016) with some modifications. Freshly obtained RBCs were washed thrice with PBS (pH 7.4). The haemolysis assay was performed at 2% hematocrit with two-fold serial dilutions from 0.1 mg/ml of test compounds in a final volume of 200 µl, followed by incubation at 37° C. for 1 h. 1% Triton-X (v/v) was used as a positive control. Non-specific haemolysis was corrected for by using untreated RBCs as negative control. After incubation, the plates were centrifuged at 2000 rpm for 5 min and the absorbance of the supernatant was measured at 540 nm using a spectrophotometric plate reader (Tecan Sunrise, Switzerland) to measure the amount of haemoglobin released upon RBC lysis. The percentage of haemolysis was calculated as follows: [(Optical density $(OD)_{540}$ of sample–$OD_{540}$ of PBS)/($OD_{540}$ of 1% Triton X-100–$OD_{540}$ of PBS)]×100. The compounds were tested in triplicates. Ethics approval for this study was obtained from the Institutional Review Board, National University of Singapore (IRB protocol reference: B-14-056).

J. Results and Discussion

J.1 Anti-Malarial Activity of Extracts from Alkaloidal Extraction

From the extraction, hexane, DCM, butanol, and aqueous extracts were obtained and screened for activity. Of the various extracts, only extracts obtained from maceration in 95% ethanol and the DCM extract (0.05% yield) from the alkaloidal extraction of Plant *Clausena lansium* showed significant antimalarial activity against *Plasmodium falciparum* 3D7, with an $IC_{50}$ of 15.01±3.19 and 13.33±5.03 µg/ml respectively.

From the ethanolic maceration extract, two most active fractions were obtained from column chromatography: fraction A which was eluted using 100% hexane-10% DCM in hexane and fraction B which was eluted using 100% DCM-15% methanol in DCM. Three independent column fractionations (column chromatography) (Plant C (*Clausena lansium*) Batch 2, Batch 5, Batch 6 in Table 3) were carried out on different batches of ethanolic maceration of Plant C leaves. The two active fractions A and B were consistently obtained from the bioassay-guided fractionation of these three extracts. Therefore, a fourth scaled-up extraction was performed by ethanolic maceration (Plant C Batch 8) and fractionated to obtain greater quantities of these two active fractions (again with consistent antiplasmodial activities) for isolation work.

The active DCM alkaloidal extract and Fraction B from the active ethanolic maceration extract were therefore subjected to fractionation using column chromatography, with the resulting isolation of compound 1.

TABLE 3

Yields and $IC_{50}$ of active Plant C (*Clausena lansium*) extracts and fractions

| Sample (Mass loaded) | Fraction | Elution gradient | Mass (g) | Yield (% w/w) | $IC_{50}$ (in µg/ml) against *P. falciparum* (n = 3) 3D7 | Dd2 |
|---|---|---|---|---|---|---|
| Chloroquine | NA | NA | NA | NA | $1.28 \pm 0.14 \times 10^{-2}$ (24.37 nM) | $0.16 \pm 0.04$ (0.31 µM) |
| Artesunate | NA | NA | NA | NA | $6.93 \pm 1.11 \times 10^{-4}$ (1.80 nM) | $2.11 \pm 0.68 \times 10^{-3}$ (5.48 nM) |

TABLE 3-continued

Yields and IC$_{50}$ of active Plant C (*Clausena lansium*) extracts and fractions

| Sample (Mass loaded) | Fraction | Elution gradient | Mass (g) | Yield (% w/w) | IC$_{50}$ (in µg/ml) against *P. falciparum* (n = 3) | |
|---|---|---|---|---|---|---|
| | | | | | 3D7 | Dd2 |
| 95% ethanol extract from maceration (NA) | NA | NA | NA | NA | 15.01 ± 3.19 | NS |
| Plant C Batch 2 (11 g) | 7-34 | 95% hexane | 0.016 | 0.003 | 2.97 ± 1.17 | ND |
| | 115-118 | 5% methanol in DCM | 0.915 | 0.15 | 5.24 ± 1.94 | ND |
| Plant C Batch 5 (6.7 g) | 10-20 | 80-90% hexane | 0.111 | 0.008 | 2.89 ± 0.30 | ND |
| | 123-166 | 100% DCM - 15% methanol in DCM | 0.422 | 0.03 | 5.52 ± 1.05 | ND |
| Plant C Batch 6 (17 g) | 10-15 | 90-100% hexane | 0.088 | 0.008 | 2.13 ± 0.49 | ND |
| | 206-209 | 100% DCM - 2% methanol in DCM | 0.119 | 0.011 | 8.92 ± 0.85 | ND |
| Plant C Batch 8 (66 g) | 1-9 | 100% hexane | 0.428 | NA | Fraction 1-2: 3.23 ± 0.37 Fraction 3-5: 1.27 ± 0.21 Fraction 6-9: 3.82 ± 0.79 As a combined fraction: 8.17 ± 1.42 | 2.36 ± 0.34 |
| | 183-194 | 1-2% methanol in DCM | 1.132 | NA | 8.09 ± 2.3 | 4.33 ± 0.5 |
| Plant C DCM extract from alkaloidal extraction (NA) | NA | NA | NA | NA | 13.33 ± 5.03 | ND |
| Plant C DCM extract from alkaloidal extraction (1.4 g) | 29-32 | 40-70% hexane | 0.0078 | 0.0017 | Not done in view of low yield | ND |
| | 63-65 | 3-5% methanol in DCM | 0.0495 | 0.011 | 8.13 ± 2.27 | ND |

NA: Not applicable; ND: Not determined; NS: Not significant.

J.2 Isolation and Chemical Analyses of Compound 1

Compound 1 (white crystalline needles, 14.4 mg, 1.03% yield) eluted at a gradient of 75% DCM in hexane while fractionating the DCM extract from alkaloidal extraction of Plant C leaves. It was also isolated after repeated fractionation and purified by recrystallization from the active fraction of the ethanolic maceration extract of Plant C leaves, eluting at 100% DCM to 5% methanol in DCM. It was washed with hexane to remove impurities. It is soluble in chloroform, acetone and dichloromethane. The following subsections discuss the chemical analyses and structural elucidation of compound 1.

J.2.1 High Performance Liquid Chromatography (HPLC)

Figure 1B:
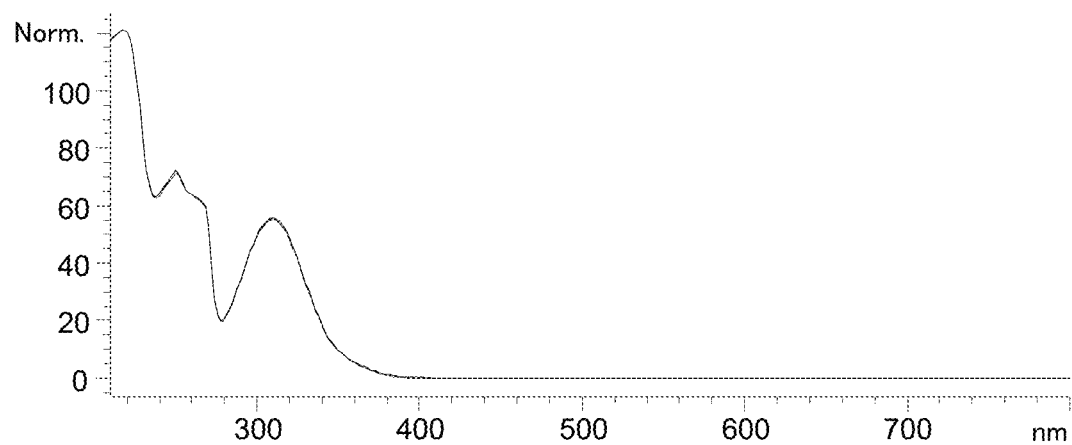
FIG. 1b shows the UV spectral overlay of the peaks at retention time of 43 min from crude Plant *Clausena lansium* extract, dichloromethane extract and compound (1b).
Figure 2:
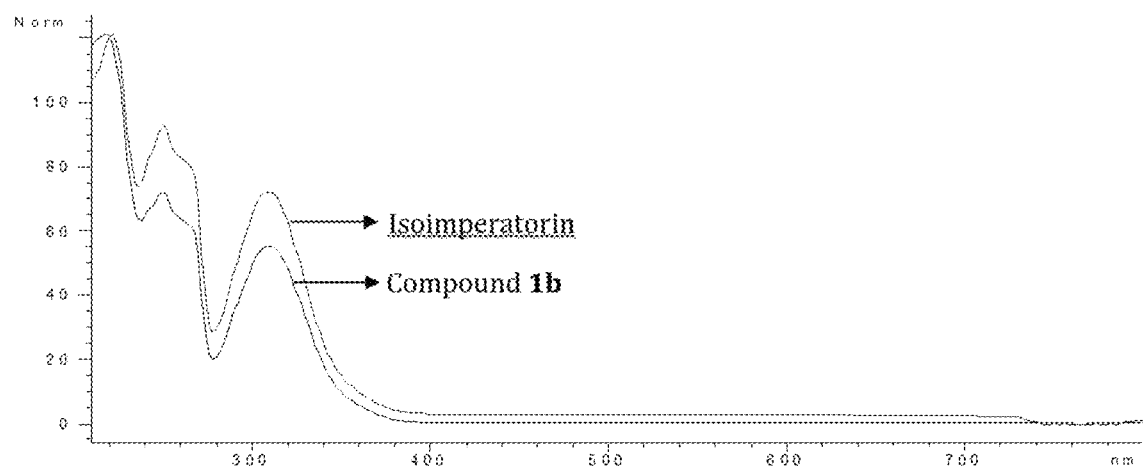
FIG. 2 shows the UV spectra of isoimperatorin and compound (1b).

Compound (1) was found to have identical retention time and UV spectra as one of the peaks in the crude extract, the DCM alkaloidal fraction and active Fraction B, as shown in FIG. 1. With the aid of an in-house UV spectral library, the UV spectrum of Compound (1) ($\lambda_{max}$ (MeOH): 218.4, 243.6, 249.9, 266.0, 310.2) was shown to closely match that of isoimperatorin, a linear furanocoumarin (match factor 978) (FIG. 2). However, compound 1 and isoimperatorin eluted at different retention times. Nevertheless, the data shows that compound 1 is likely to contain a linear furanocoumarin core.

J.2.2 Gas Chromatography-Mass Spectrometry (GC-MS)

Figure 3:
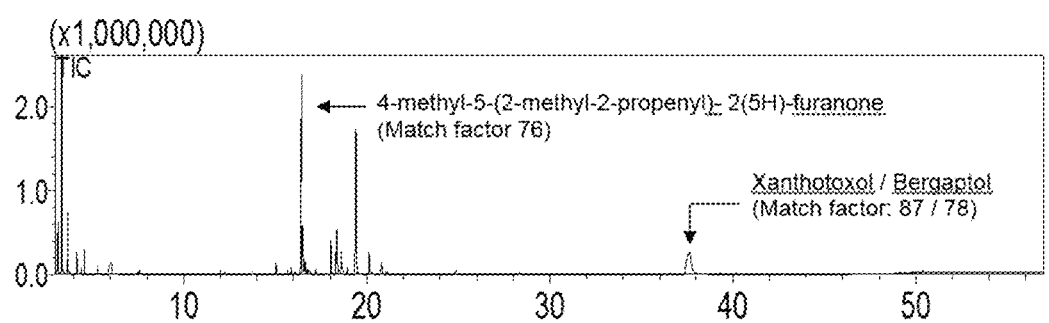
FIG. 3 shows the gas chromatography-mass spectrometry (GC-MS) profile of compound (1b).

GC-MS results of compound 1 are shown in FIG. 3. The small peak at 37.8 min had match factors of 87 and 78 with xanthotoxol and its isomer bergaptol respectively, both of which are linear furanocoumarins. The peak at 16.4 min had a match factor of 76 with 4-methyl-5-(2-methyl-2-propenyl)-2(5H)-furanone. These results were in line with HPLC results and suggested that compound 1 had a furanocoumarin core with a methylfuranone derivative.

J.2.3 Fourier-Transform Infrared Spectroscopy (FT-IR) and High Resolution Electrospray Ionization Mass Spectrometry (HREIMS)

Figure 4:
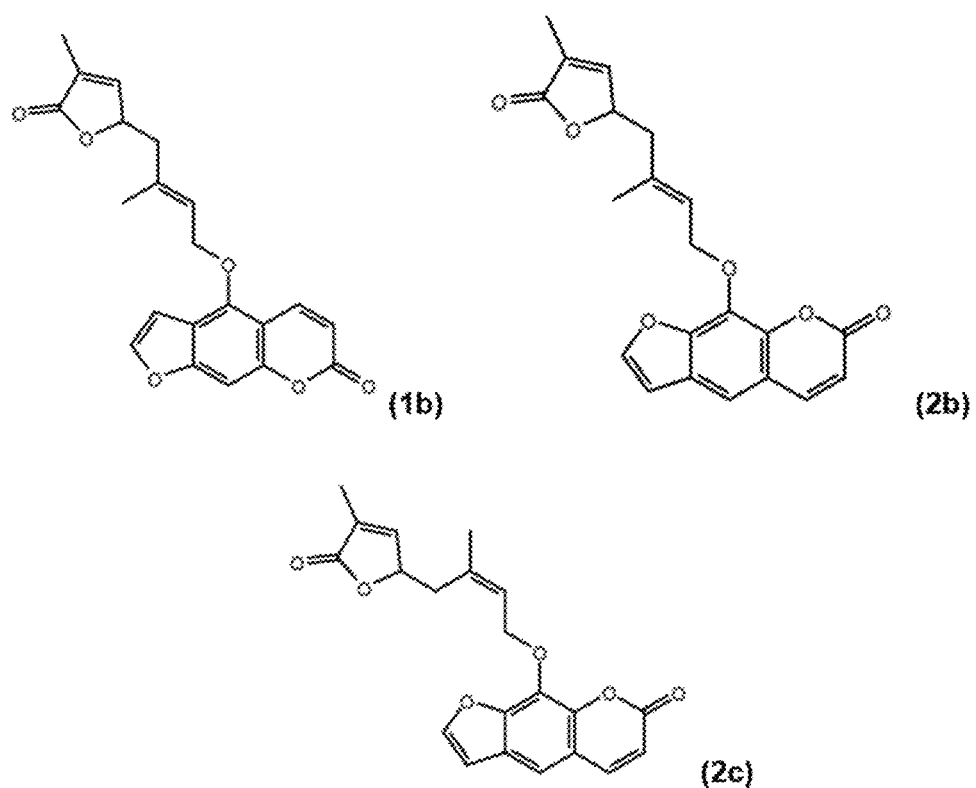
FIG. 4 shows the structures of (1b) anisolactone, (2b) wampetin and (2c) indicolactone.

Compound 1 showed IR bands at 1761 and 1723 cm$^{-1}$, which indicated the presence of α,β-unsaturated γ- and δ-lactones respectively. From HREIMS, the protonated molecular ion [M+H]$^+$ has an m/z of 367.11783, with a sodium adduct [M+Na]$^+$ at m/z 369.09937. Therefore the molecular ion with a mass of 366 was analysed for $C_{21}H_{18}O_6$. A literature search revealed the possible identity of compound 1 as either anisolactone, wampetin, indicolactone, all of which are isomers of each other (FIG. 4).

Figure 5:
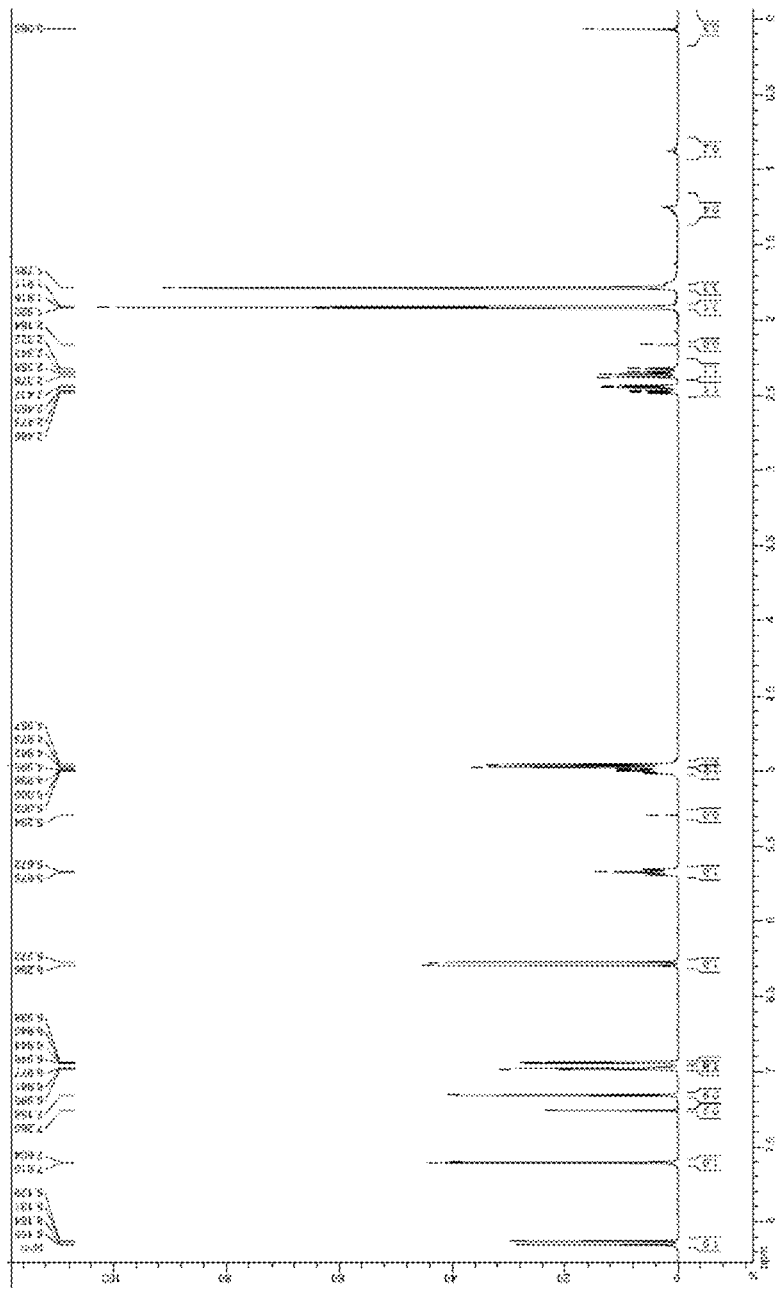
FIG. 5 shows the $^1$H NMR (Nuclear Magnetic Resonance) spectrum of compound (1b).
Figure 6:
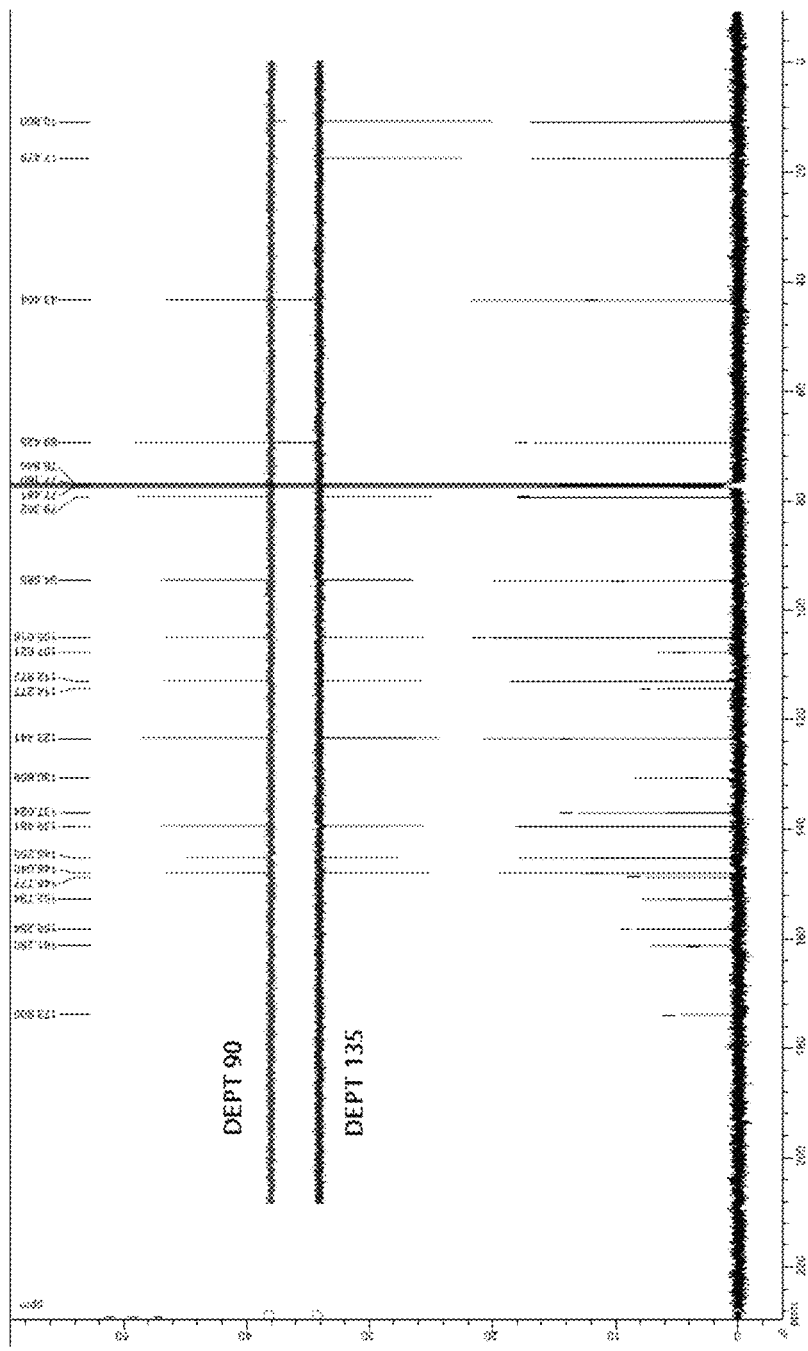
FIG. 6 shows the $^{13}$C NMR spectra including Distortionless Enhancement by Polarization Transfer spectra (both DEPT 90 and DEPT 135) of compound (1b).
Figure 7:
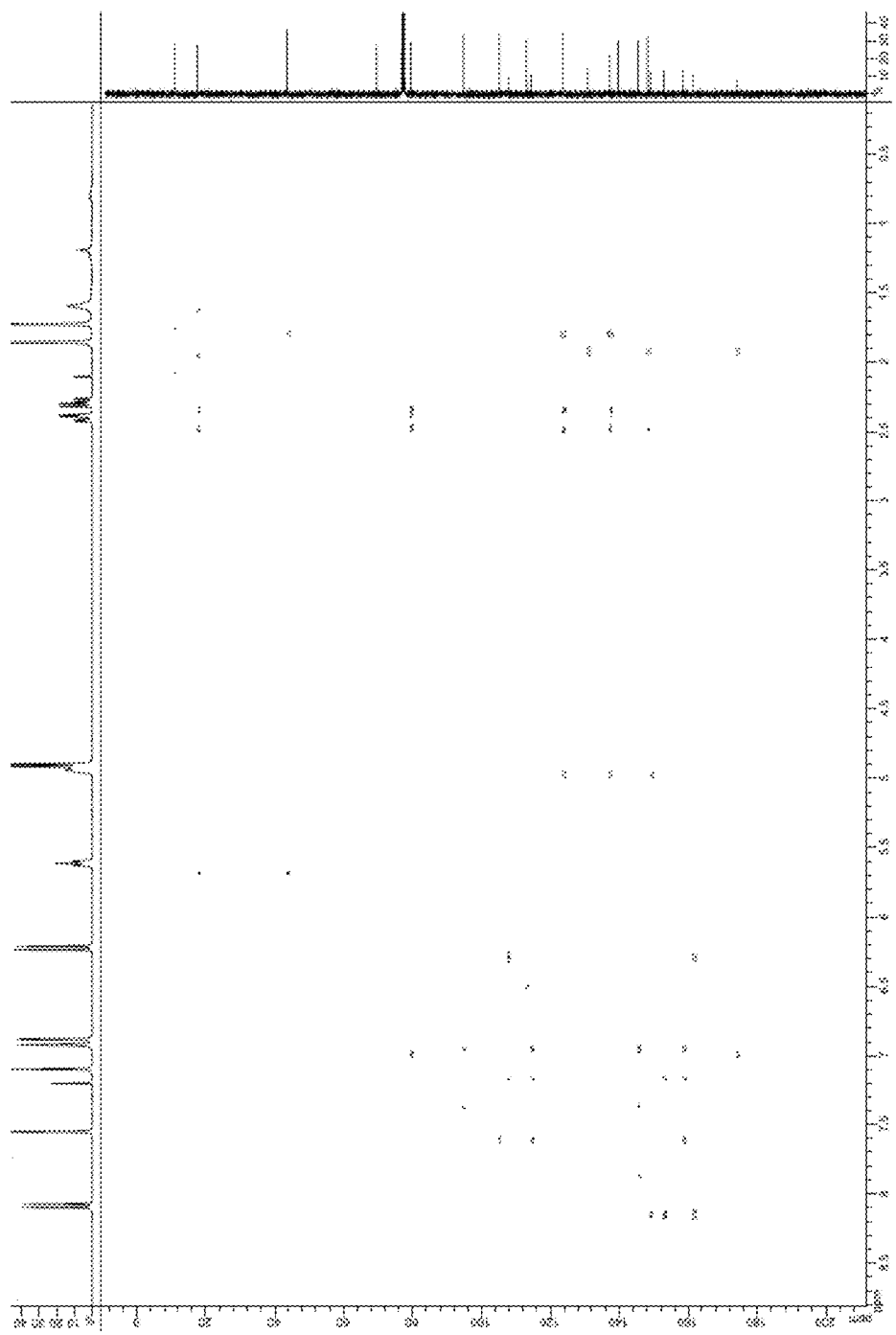
FIG. 7 shows the Heteronuclear Multiple Bond Correlation (HMBC) spectrum of compound (1b).
Figure 8:
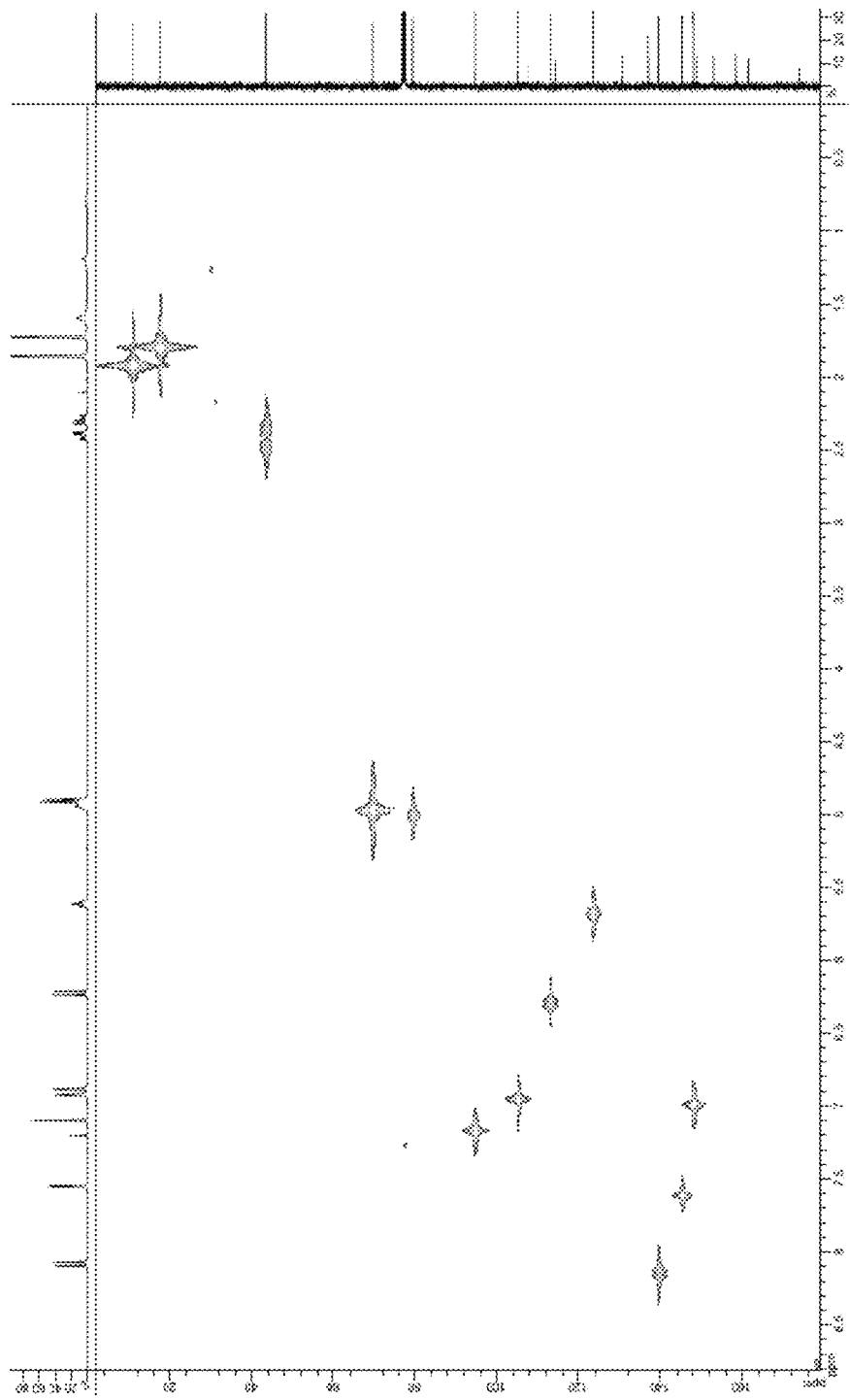
FIG. 8 shows the Heteronuclear Multiple Quantum Coherence (HMQC) spectrum of compound (1b).

J.2.4 Nuclear Magnetic Resonance (NMR) Spectroscopy $^1$H (FIG. 5), $^{13}$C (FIG. 6), DEPT 90 (FIG. 6), and DEPT 135 (FIG. 6) were used to determine the structure of compound 1. Protons and carbon connectivity correlations were assigned Using Heterenuclear Multiple Quantum Coherence (HMQC, FIG. 8). Quaternary and non-protonated carbons were assigned using Heteronuclear Multiple Bond Correlation (HMBC, FIG. 7). The NMR data for compound 1 are as follow:

$^1$H NMR (400 MHz, CDCl$_3$), δ 1.79 (3H, s, Me, H-4'), 1.92 (3H, t, J=3.5 Hz, Me, H-9'), 2.41 (2H, dq, J=58.9 Hz, H-5'), 4.96 (2H, d, J=6.5 Hz, H-1'), 5.00 (1H, m, H-6'), 5.67 (1H, dt, J=13.4 Hz, H-2'), 6.28 (1H, d, J=9.8 Hz, H-5), 6.94 (1H, dd, J=3.3 Hz, H-7'), 6.96 (1H, m, J=6.4 Hz, H-3), 7.16 (1H, s, H-9), 7.61 (1H, d, J=2.4 Hz, H-2), 8.14 (1H, d, J=9.8 Hz, H-6).

$^{13}$C NMR (100 MHz, CDCl$_3$), δ 10.80 (C-9'), 17.48 (C-4'), 43.40 (C-5'), 69.43 (C-1'), 79.36 (C-6'), 94.59 (C-9), 105.02 (C-7'), 107.62 (C-12), 112.97 (C-5), 114.28 (C-11), 123.44 (C-2'), 130.66 (C-8'), 137.02 (C-3'), 139.48 (C-6), 145.26 (C-2), 148.04 (C-3), 148.78 (C-4), 152.79 (C-8), 158.25 (C-10), 161.28 (C-7), 173.90 (C-10').

As the natural product anisolactone has only ever been found in very small quantities in the past such analysis has never been feasible. As such this is the first report of the detailed structure of anisolactone. This is also the first report of $^{13}$C NMR data for anisolactone.

Taking into consideration all data on compound 1, together with comparison of literature data, the identity of compound 1 was confirmed to be anisolactone (FIG. 4, 1b). Its melting point was determined to be 155.1° C.-155.7° C.

J.3 Cytotoxicity and Selectivity Indices of Active Samples and Compounds from Plant C Leaves Table 4 summarizes the 50% cytotoxicity concentration (CC$_{50}$) results and selectivity indices of Plant C active samples and compounds. Anisolactone is highly selective for P. falciparum. The active fractions are moderately selective for P. falciparum [with Selective Index (SI) ranging from 12 to 22]. Although the crude ethanolic maceration extract is toxic against NL20 cells (SI of 4), the active compound anisolactone did not exhibit cytotoxic effects on host cells even at the highest concentration tested (1 mg/ml) and are also found to be less cytotoxic than artesunate and chloroquine. The results suggest that the antimalarial activity of anisolactone is possibly a direct inhibitory action on parasite rather than non-selective toxicity to host and target cells. In view that the active compound performs direct inhibitory action on parasite and its less cytotoxicity in nature, the active compound anisolactone is also potentially suitable for use in prevention of malaria.

Incorporation of a selectivity index allows for a more qualitative assessment of compounds that are genuinely promising as antimalarial leads by differentiating true antiplasmodial activity from non-specific toxicity (Pezzuto et al. 1997; Cos et al. 2006). There are no standard cut-off values for categorizing selectivity although in general, a true pharmacological effect is distinguished from non-selective toxicity when SI>10 (Weniger et al. 2001, Irungu et al. 2015). The current findings therefore provide preliminary data on the selectivity of Plant C leaf extracts and anisolactone for P. falciparum.

TABLE 4

Cytotoxicity results from WST-1 assay and selectivity indices of active samples and compounds from Plant C

| Sample | CC$_{50}$ against NL20 (μg/ml) | IC50 against P. falciparum 3D7 (μg/ml) | SI |
|---|---|---|---|
| Chloroquine | 94.04 ± 2.44 | 0.012753 | 7374 |
| Artesunate | 5.63 ± 0.82 | 0.0006933 | 8123 |
| Plant C ethanolic maceration extract | 56.47 ± 10.3 | 15 | 4 |
| Fraction A (Plant C Batch 36, 5-41) | 151.60 ± 28.05 | 2.84 | 53 |
| Fraction B (Plant C Batch 8, 183-194) | 100.70 ± 3.44 | 8.09 | 12 |
| Plant C DCM alkaloidal extract | 286.10 ± 29.10 | 13.3 | 22 |
| Anisolactone | NA (not cytotoxic at the highest concentration studied, i.e. 1 mg/ml) | 7.5 | NA |

NA. Not applicable.

J.4 Haemolysis Potential of Anisolactone

Table 5 shows the results of the haemolysis assay, normalized to 100% lysis in the positive control. Anisolactone did not cause significant haemolysis at the concentrations tested, including the highest concentration of 0.1 mg/ml (prepared in phosphate buffered saline (PBS)) which is more than 10 times their IC$_{50}$ values. The concentration of 0.1 mg/ml was chosen as the highest concentration for this assay. Visual inspection of the well plates indicated that treatment with anisolactone had similar effects as untreated Red Blood Cells (RBCs) since in both cases, the RBCs formed a pellet at the bottom of the well with clear colourless supernatant. In the positive control, the supernatant was red and there was no pellet formed due to RBC lysis. Results suggest that the antiplasmodial activity of anisolactone is not due to RBC lysis but a direct inhibitory action on the Plasmodium parasite instead. This is the first study demonstrating the lack of toxicity of anisolactone in normal human RBCs.

TABLE 5

Haemolysis potential of anisolactone

| Compound | % Haemolysis (n = 3) |
|---|---|
| 1% Triton X-100 (Positive Control) | 100 |
| Untreated RBCs | 0.46 ± 0.31 |
| Anisolactone (0.1 mg/ml) | 0.99 ± 0.28 |

In this study, compound 1 (anisolactone) was found to have novel and significant antiplasmodial activity against P. falciparum, with IC$_{50}$ of 7.50 μg/ml (20.5 μM). It showed high selectivity for the parasite, as seen from its low toxicity profiles against NL20 and human RBCs. The anti-malarial activity of anisolactone has not been reported. Additionally, this is also the first report of the $^{13}$C NMR data for anisolactone.

Bioassay-guided fractionation has been successfully performed on the two active extracts of Plant C leaves, namely, the ethanolic maceration extract and the DCM extract obtained from alkaloidal extraction, resulting in the isolation of anisolactone. This is the first report of the antimalarial activity of anisolactone and the first study showing the lack of toxicity of this compound on normal uninfected human red blood cells.

The invention claimed is:

1. A method of treating a malaria in a subject, comprising administering to the subject a pharmaceutical composition consisting of a furanocoumarin derivative having the following core structure (A),

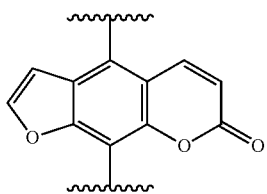

(A)

or its pharmaceutical acceptable salt, wherein the furanocoumarin derivative is anisolactone having structure (1b):

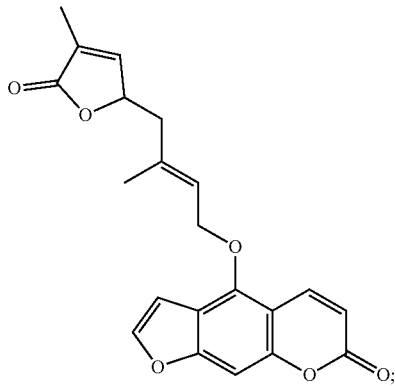

(1b)

and
wherein the anisolactone is isolated from a plant comprising a *Clausena lansium* species, the isolated anisolactone is purified by recrystallization to form an isolated purified anisolactone, and
wherein the administering of the pharmaceutical composition comprises a therapeutically effective amount of the isolated purified anisolactone,
wherein the therapeutically effective amount comprises 7.50 micrograms/milliliter of anisolactone.

2. The method according to claim 1, wherein the malaria is transmitted by an arthropod.

3. The method according to claim 2, wherein the arthropod comprises an *Anopheles* genus.

4. The method according to claim 1, wherein the malaria is caused by a *Plasmodium* parasite.

5. The method according to claim 4, wherein the *Plasmodium* parasite is a *Plasmodium falciparum*.

6. The method according to claim 1, wherein the subject is a human.

7. The method according to claim 1, wherein the route of administration is oral, intravenous, sublingual, subcutaneous or intramuscular.

* * * * *